(12) United States Patent
Huxel et al.

(10) Patent No.: US 11,103,353 B2
(45) Date of Patent: Aug. 31, 2021

(54) ANKLE PROSTHESIS AND METHODS OF USING THE SAME

(71) Applicant: DT MEDTECH LLC, Baltimore, MD (US)

(72) Inventors: Shawn Thayer Huxel, Seaside Park, NJ (US); John S. Crombie, East Hanover, NJ (US); Beat Hintermann, Liestal (CH); Andrew R. Fauth, North Logan, UT (US); Justin Hyer, Smithfield, UT (US); Zachary C. Christensen, Wellsville, UT (US); Trevor K. Lewis, Lehi, UT (US); Nathan O. Plowman, Wellsville, UT (US); Neil Etherington, North Logan, UT (US); David Koch, North Logan, UT (US)

(73) Assignee: DT MEDTECH, LLC, McMinnville, TN (US)

( * ) Notice: Subject to any disclaimer, the term of this patent is extended or adjusted under 35 U.S.C. 154(b) by 547 days.

(21) Appl. No.: 15/707,661

(22) Filed: Sep. 18, 2017

(65) Prior Publication Data
US 2018/0125663 A1    May 10, 2018

Related U.S. Application Data

(60) Provisional application No. 62/395,781, filed on Sep. 16, 2016.

(51) Int. Cl.
*A61F 2/42* (2006.01)
*A61F 2/30* (2006.01)
*A61F 2/46* (2006.01)

(52) U.S. Cl.
CPC ............ *A61F 2/30771* (2013.01); *A61F 2/42* (2013.01); *A61F 2/4202* (2013.01); *A61F 2/46* (2013.01);
(Continued)

(58) Field of Classification Search
CPC ....... A61F 2/30771; A61F 2/42; A61F 2/4202
See application file for complete search history.

(56) References Cited

U.S. PATENT DOCUMENTS

| 8,668,743 B2 * | 3/2014 | Perler | A61F 2/4202 623/21.18 |
| 9,610,168 B2 * | 4/2017 | Terrill | A61F 2/4202 |

(Continued)

FOREIGN PATENT DOCUMENTS

| WO | WO 2011/101699 | 8/2011 |
| WO | WO 2011/150148 | 12/2011 |
| WO | WO 2014/179589 | 11/2014 |

OTHER PUBLICATIONS

DT Medtech, LLC, International Search Report and Written Opinion for PCT/US2017/052089 dated Dec. 8, 2017, 18 pages.

*Primary Examiner* — Bruce E Snow
*Assistant Examiner* — Melissa A Hoban
(74) *Attorney, Agent, or Firm* — Reed Smith LLP; Matthew P. Frederick; John M. Cogill

(57) ABSTRACT

The present disclosure pertains to ankle prostheses. In an example embodiment, the ankle prosthesis comprises an adjustable and replaceable intermediate implant that is disposed between a tibial implant and a talar implant. The intermediate implant is adjustable relative to the tibial implant and can be interlocked therewith once adjusted. Methods of using, fitting, and adjusting the device are also described. Still other embodiments are described.

20 Claims, 17 Drawing Sheets

(52) U.S. Cl.
CPC .............. *A61F 2/4684* (2013.01); *A61F 2/30* (2013.01); *A61F 2/4606* (2013.01); *A61F 2002/3054* (2013.01); *A61F 2002/3071* (2013.01); *A61F 2002/3093* (2013.01); *A61F 2002/30205* (2013.01); *A61F 2002/30331* (2013.01); *A61F 2002/30367* (2013.01); *A61F 2002/30395* (2013.01); *A61F 2002/30405* (2013.01); *A61F 2002/30482* (2013.01); *A61F 2002/30485* (2013.01); *A61F 2002/30507* (2013.01); *A61F 2002/30537* (2013.01); *A61F 2002/30578* (2013.01); *A61F 2002/30604* (2013.01); *A61F 2002/30607* (2013.01); *A61F 2002/30614* (2013.01); *A61F 2002/30616* (2013.01); *A61F 2002/30617* (2013.01); *A61F 2002/30708* (2013.01); *A61F 2002/30785* (2013.01); *A61F 2002/30841* (2013.01); *A61F 2002/30845* (2013.01); *A61F 2002/30929* (2013.01); *A61F 2002/30935* (2013.01); *A61F 2002/4205* (2013.01); *A61F 2002/4207* (2013.01); *A61F 2002/4619* (2013.01); *A61F 2002/4622* (2013.01); *A61F 2002/4658* (2013.01); *A61F 2310/00407* (2013.01); *A61F 2310/00796* (2013.01)

(56) References Cited

U.S. PATENT DOCUMENTS

| | | | |
|---|---|---|---|
| 10,327,905 B2 * | 6/2019 | Rouyer | A61F 2/4202 |
| 2006/0229730 A1 * | 10/2006 | Railey | A61B 17/15 623/21.18 |
| 2007/0100463 A1 * | 5/2007 | Aram | A61F 2/389 623/20.29 |
| 2008/0103603 A1 | 5/2008 | Hintermann | |
| 2013/0041473 A1 * | 2/2013 | Rouyer | A61F 2/4202 623/21.18 |

\* cited by examiner

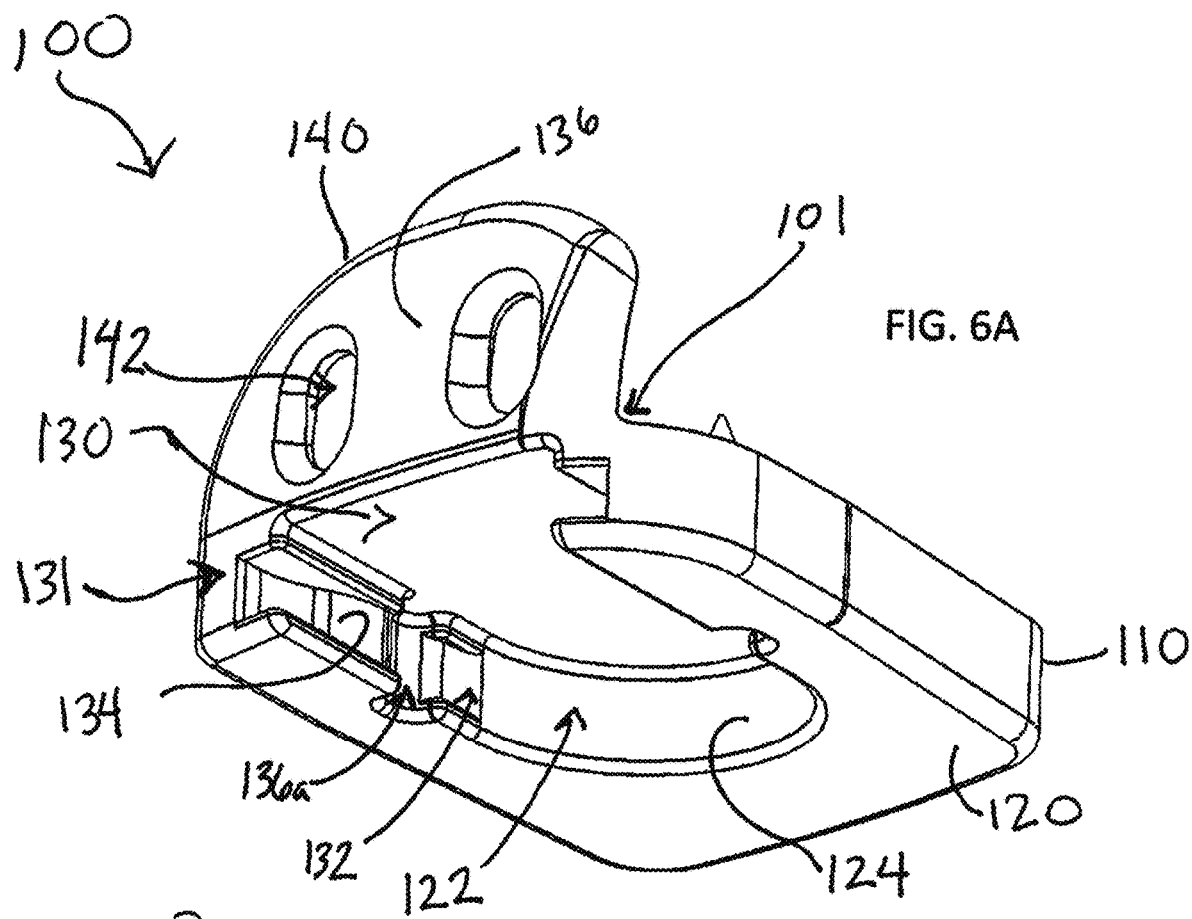
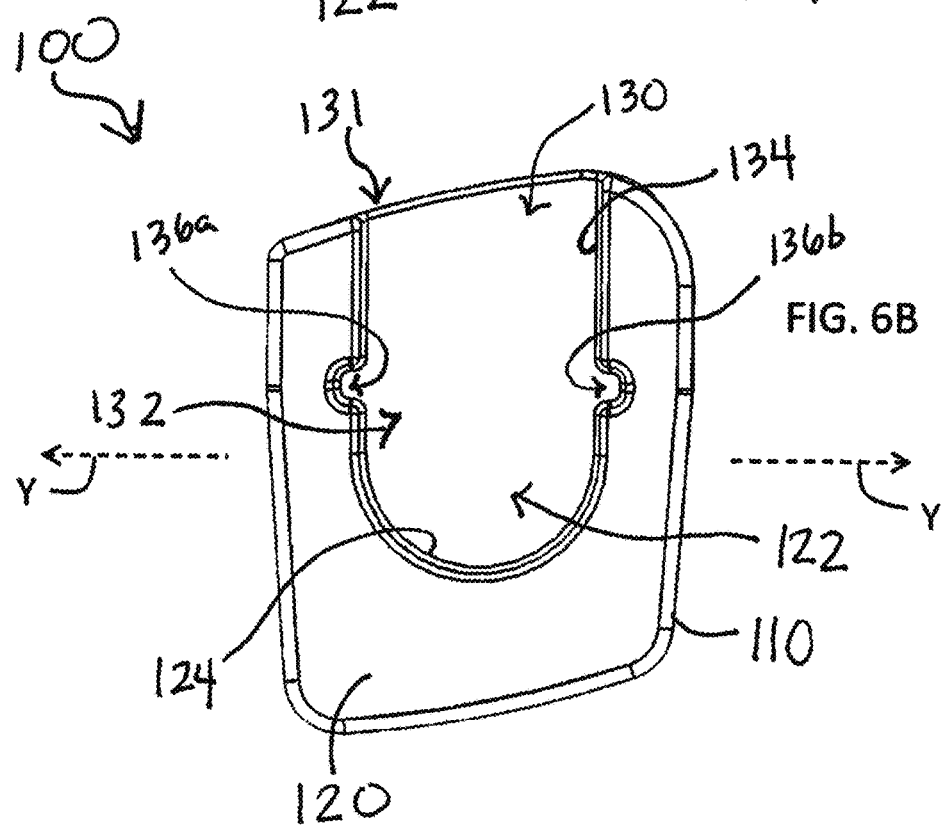

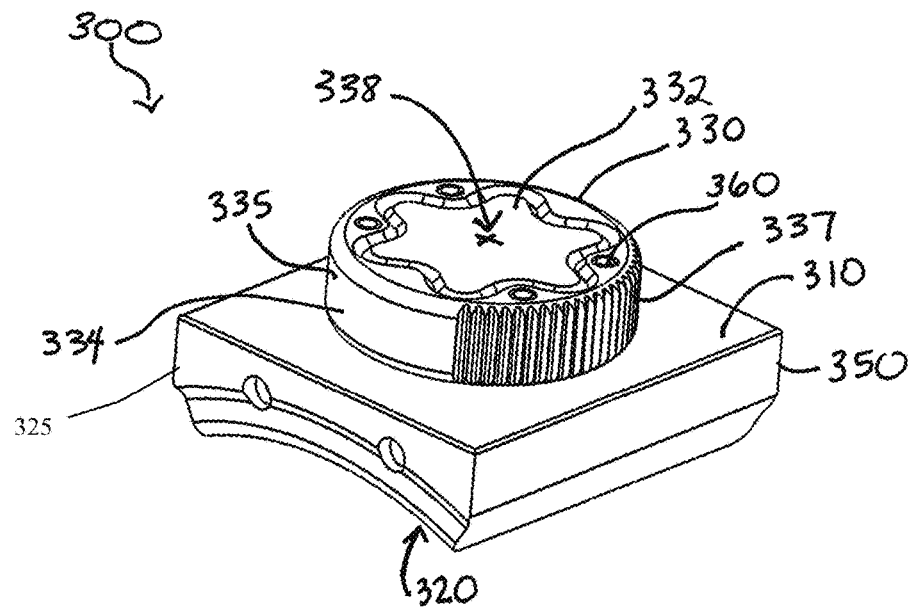
FIG. 8A
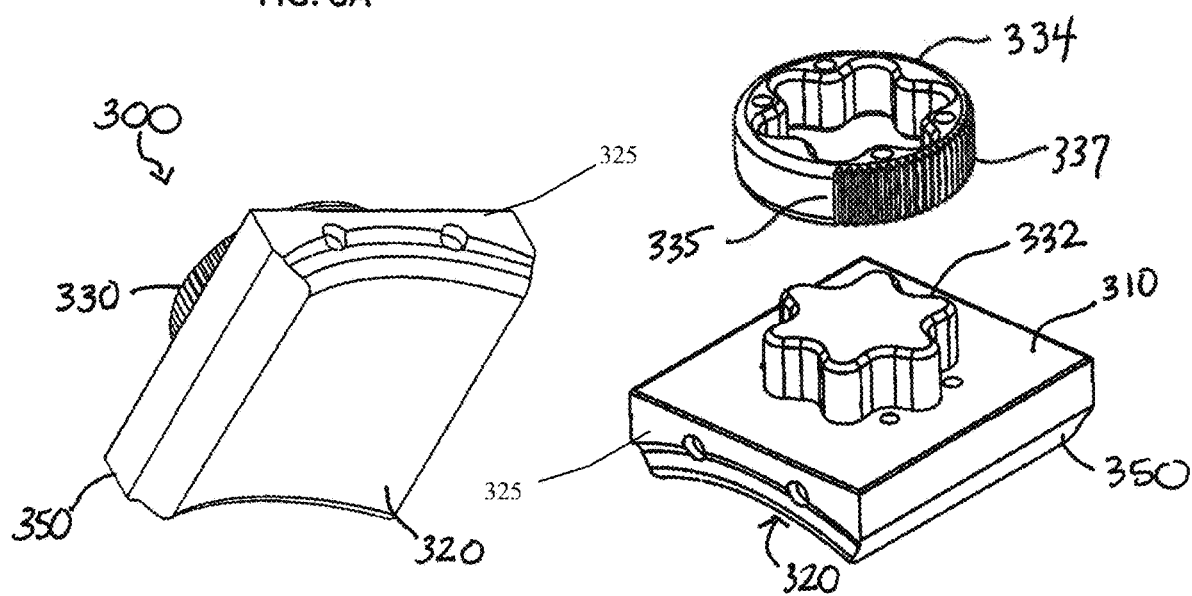
FIG. 8B
FIG. 8C

ANKLE PROSTHESIS AND METHODS OF USING THE SAME

CROSS REFERENCE TO RELATED APPLICATION

This application claims priority to U.S. Provisional Application No. 62/395,781, filed Sep. 16, 2016. The contents of which are incorporated by reference in their entirety.

TECHNICAL FIELD

The present application relates to the technical field of joint prostheses, and more particularly to orthopedic implants facilitating at least some restoration in anatomical mobility to a joint, such as an ankle joint.

BACKGROUND

Joint prostheses can be used to restore a certain amount of freedom of movement to a joint, after the joint has been damaged due to injury or disease. For example, ankle joints can be damaged by arthritis, and an ankle replacement joint prosthesis can bring such patients a reduction in pain and improvement in mobility.

Ankle prosthesis are designed to replace the ankle joint and replicate the anatomic motion of the ankle joint which includes loadbearing and flexion of the foot through the gait cycle. Flexion of the foot includes dorsi-flexion, or upward motion of the forefoot relative to the hindfoot, and plantar-flexion, downward motion of the forefoot relative to the hindfoot. As the foot flexes, minor rotation, internal for dorsi-flexion and external for plantar-flexion must occur between the foot and the tibia. To account for this complex dynamic motion, optimally, the prosthetic joint would be located such that the load-bearing central axis of the tibia is aligned with the apex of the talar dome. In addition, such a joint would not be cylindrical, but would form the partial surface of a cone. This frustoconical surface is defined by locating the smaller radius of the cone on the interior side of the ankle (the lateral side closer to the median axis of the body) and the larger radius on the outer side of the ankle (the lateral side further from the median axis of the body).

Insertion of an ankle prosthesis includes providing surgical access to the joint being replaced, preparing the surfaces of the distal tibia and the talar dome for acceptance of the prosthesis, and providing just enough space for the prosthesis for fit and function. Generally, a diseased ankle, even when surgically prepared to accept a prosthesis, would be mal-aligned to accept the prosthesis "out of the box". Therefore, certain surgical intervention would be necessary to balance the ankle joint including, but not limited to, osteotomies (in order to shorten, lengthen, or reorient bones), soft tissue excision (in order to alleviate unwanted tension to the skeletal structure), or the support or tightening of soft tissue (in order to add tension and support to the skeletal structure). Even in the best of surgical hands, the ankle prosthesis would still have to support loading which may not be matched to the perfect anatomy of the complex healthy ankle joint. Thus, an ankle prosthesis which is adaptable to the variations of the anatomy and of the surgical placement of the fixed components of the prosthesis would be beneficial to restoring motion of the replaced ankle joint.

Ankle prostheses are composed of components moveable relative to each other, such as a talar implant, a tibial implant, and an intermediate implant interposed between said tibial implant and said talar implant. The intermediate implant and the talar implant can move relative to each other. In certain ankle prostheses, the tibial implant and the intermediate implant are fixed relative to each other.

Once surgical access is achieved and the ankle joint is balanced and prepared to accept the prosthesis, the tibial implant and the talar implant are fixed to the bones of the tibia and the talus, respectively. In most surgical instances, the center of the tibia implant may or may not be aligned with the central axis of the tibia bone and the talar implant may be rotated, internally or externally, relative to the central axis of the tibia bone. In addition, the center of the tibial implant may not be aligned with the apex of the talar implant to provide and maximize full flexion of the foot.

Current ankle prostheses available are either (i) "mobile bearing" in that the intermediate implant to tibia implant interface is a planar friction joint allowing for anterior-posterior and lateral translation, coupled with relatively free internal and external rotation of the intermediate implant relative to the tibial implant; or (ii) "semi-constrained" in that the intermediate implant is fixed to the tibial implant in a predetermined fashion (referred to herein as "fixed bearing" as well), regardless of the anatomic placement of the tibial implant relative to the talar implant.

The mobile-bearing design, due to its relatively low level of constraint, accommodates variability in anatomy and surgical placement of the tibial and talar implants. However, the lack of constraint introduces circumstances requiring significant surgical skill in placing the implant while balancing the skeletal and soft tissue anatomy about the ankle prosthesis. Anatomic balancing is required in order to prevent subluxation or, sometimes, fracture of the mobile-bearing intermediate implant when the tibial and talar components of the prosthesis are loaded in a condition of mal-alignment. In addition, highly diseased or deformed ankles may not be candidates for the mobile-bearing design.

The semi-constrained design, due to its relatively high level of constraint, does not accommodate variability in anatomy and surgical placement of the tibial and talar implants. The intermediate implant is rigidly affixed to the tibial implant either in vitro, that is while the tibial implant and intermediate implant are outside the patient or in vivo, where the fixation of the intermediate implant takes place in the patient after implantation of the tibial implant. However, the presence of constraint introduces circumstances requiring significant surgical skill in placing the implant in that the talar and tibial implants must be expertly aligned by the surgeon utilizing techniques for balancing the skeletal and soft tissue anatomy about the ankle prosthesis. Anatomic balancing is required in order to prevent abnormal loading and subsequent wear of the fixed intermediate implant when the tibial and talar components of the prosthesis are loaded in a condition of mal-alignment. Advantages of this design, due to the constraint, include use in patients with poor soft tissue support of the ankle joint or in patients where large deformity has been corrected by the surgeon. Each of these instances require a more stable, semi-constrained prosthesis.

SUMMARY

Embodiments of the invention described herein combine the advantages of both a mobile-bearing design and a semi-constrained design to treat a broader spectrum of patients and to better adapt the implant to the patient anatomy and placement of the talar and tibial components. Further embodiments of the invention can allow for adjusting the relative position of the ankle prosthesis components, particularly, the position of an intermediate implant relative to a tibial implant, and then securely fixing these components to each other. Moreover, embodiments of this invention can allow for components, particularly the intermediate implant, to be replaced and adjusted when clinically indicated due to, for example, wear of the component.

Embodiments of the present disclosure can comprise an ankle prosthesis having a tibial implant, an intermediate implant, and an implant lock. The intermediate implant can comprise a first surface and a second, curved surface opposite the first surface and a projecting member extending outwardly from the first surface. The projecting member can be configured to extend into a recess of the tibial implant and rotate relative to the tibial implant. The implant lock can be configured to resist rotation of the projecting member relative to the tibial implant by applying a force that is substantially perpendicular to the axis of rotation of the projecting member.

Other embodiments of the present disclosure can also comprise an ankle prosthesis having a tibial implant, an intermediate implant, and an implant lock. The tibial implant can define a recess and a slot, wherein the slot is in communication with the recess. The intermediate implant can comprise a first surface and a second, curved surface opposite the first surface and a projecting member extending outwardly from the first surface. The projecting member can be configured to extend into the recess of the tibial implant and rotate relative to the tibial implant. The implant lock can be configured to be at least partially disposed within the slot and to resist rotation of the projecting member relative to the tibial implant, wherein the slot is configured such that the implant lock is inserted into the slot along a direction that is substantially perpendicular to the axis of rotation of the projecting member.

Still other embodiments of the present disclosure can also comprise an ankle prosthesis having a tibial implant, an intermediate implant, and an implant lock. The intermediate implant can comprise a first surface and a second, curved surface opposite the first surface and a projecting member extending outwardly from the first surface, wherein the projecting member is configured to be disposed in a recess of the tibial implant and rotate relative to the tibial implant. The implant lock can be configured to resist rotation of the projecting member relative to the tibial implant. The projecting member can comprise a lateral surface, and the implant lock can be configured to engage with the lateral surface of the projecting member such that rotation of the projecting member is resisted.

Still other embodiments of the present disclosure can comprise an ankle prosthesis having a talar implant, a tibial implant, and an intermediate implant. The intermediate implant can comprise a first surface and a second, curved surface opposite the first surface and a projecting member extending outwardly from the first surface. The talar implant can be configured to move relative to the to the intermediate implant along the second surface, and the projecting member can be configured to extend into a recess of the tibial implant and rotate at least 180 degrees relative to the tibial implant.

Other embodiments of the present disclosure can comprise an ankle prosthesis component having an intermediate implant. The intermediate implant can comprise a base having a first surface and a second, curved surface opposite the first surface and a projecting member extending outwardly from the first surface of the base. The projecting member can have a width and the base has a width and wherein the projecting member width is 25% to 85% of the base width.

Still other embodiments of the present disclosure can comprise a method of fixing the relative position of an intermediate implant of an ankle prosthesis, wherein the intermediate implant is configured to be disposed between a tibial implant and a talar implant, and the method can comprise rotating the intermediate implant relative to the tibial implant while the tibial implant, the talar implant, and the intermediate implant are implanted in the ankle and fixing the position of the intermediate implant relative to the tibial implant by applying a force that is substantially perpendicular to the axis of rotation of the intermediate implant.

Yet other embodiments of the present disclosure can comprise a method of replacing an intermediate implant of an ankle prosthesis, wherein the intermediate implant is configured to be disposed between a tibial implant and a talar implant, and the method can comprise releasing an implant lock of a first intermediate implant of the ankle prosthesis such that the first intermediate implant can rotate relative to the tibial implant, wherein the implant lock is released by removing a force that is substantially perpendicular to the axis of rotation of the intermediate implant; hereafter, removing the first intermediate implant from the ankle prosthesis; and inserting a second intermediate implant into the ankle prosthesis.

These and other aspects, objects, features, and embodiments will be apparent from the following description and the appended claims. Those skilled in the art may use the components of the ankle prosthesis together or separate and may apply techniques provided herein for other applications.

BRIEF DESCRIPTION OF THE DRAWINGS

The drawings illustrate only example embodiments of ankle prostheses and are therefore not to be considered limiting of its scope.

FIG. 6A illustrates a lower, perspective view of the tibial implant shown in FIG. 2.

FIG. 6B illustrates bottom view of the tibial implant shown in FIG. 2.

FIG. 8A illustrates a upper, perspective view of the intermediate implant shown in FIG. 2.

FIG. 8B illustrates a lower, perspective view of the intermediate implant shown in FIG. 2.

FIG. 8C illustrates an exploded view of the intermediate implant shown in FIG. 2.

FIG. 10C illustrates the implant lock in an unlocked position with the intermediate implant. FIG. 10D illustrates the implant lock in an interlocking position with the intermediate implant.

DETAILED DESCRIPTION OF EXAMPLE EMBODIMENTS

Figure 1:
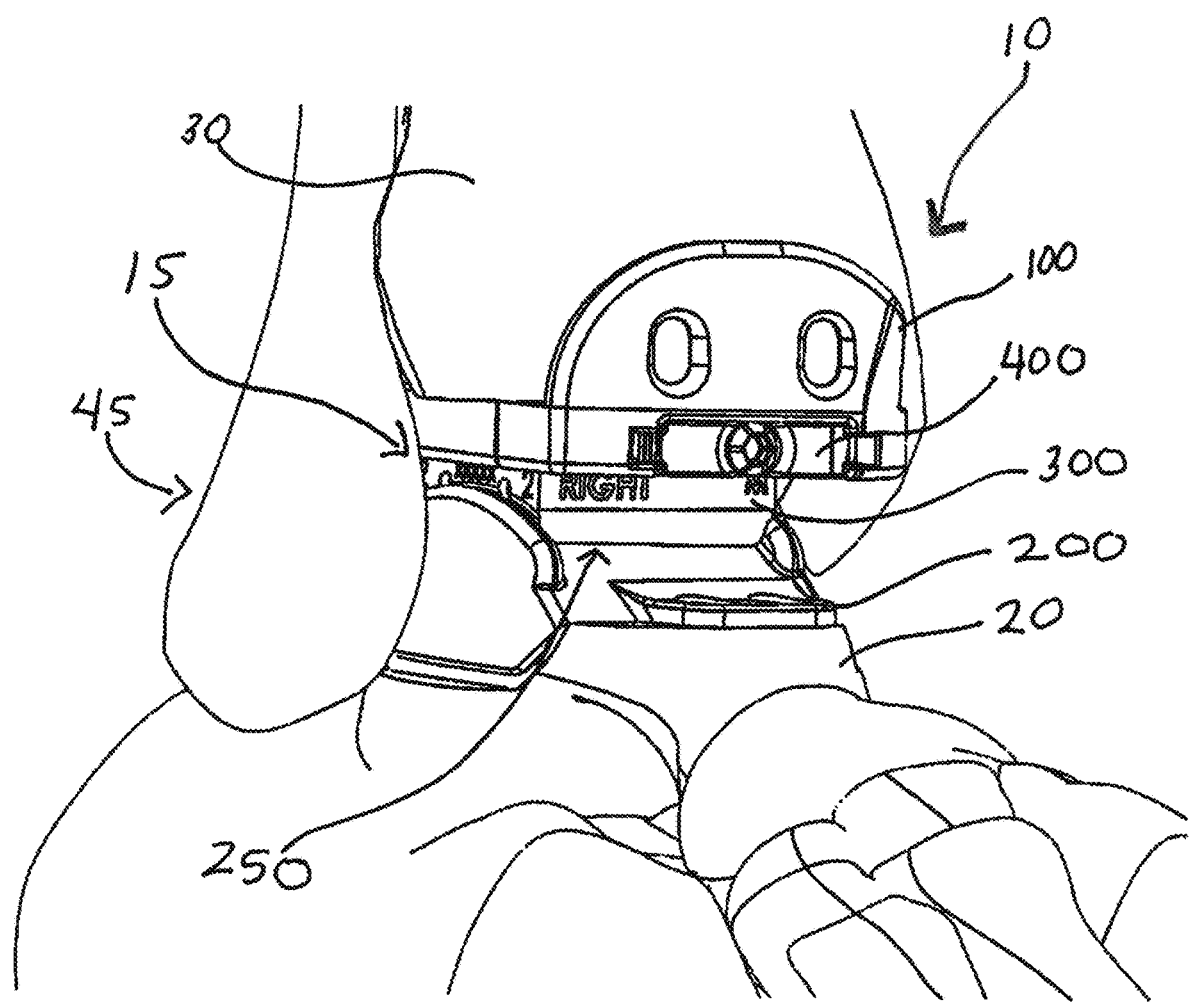
FIG. 1 illustrates an embodiment of an ankle prosthesis implanted in an ankle in accordance with the present disclosure.
Figure 2:
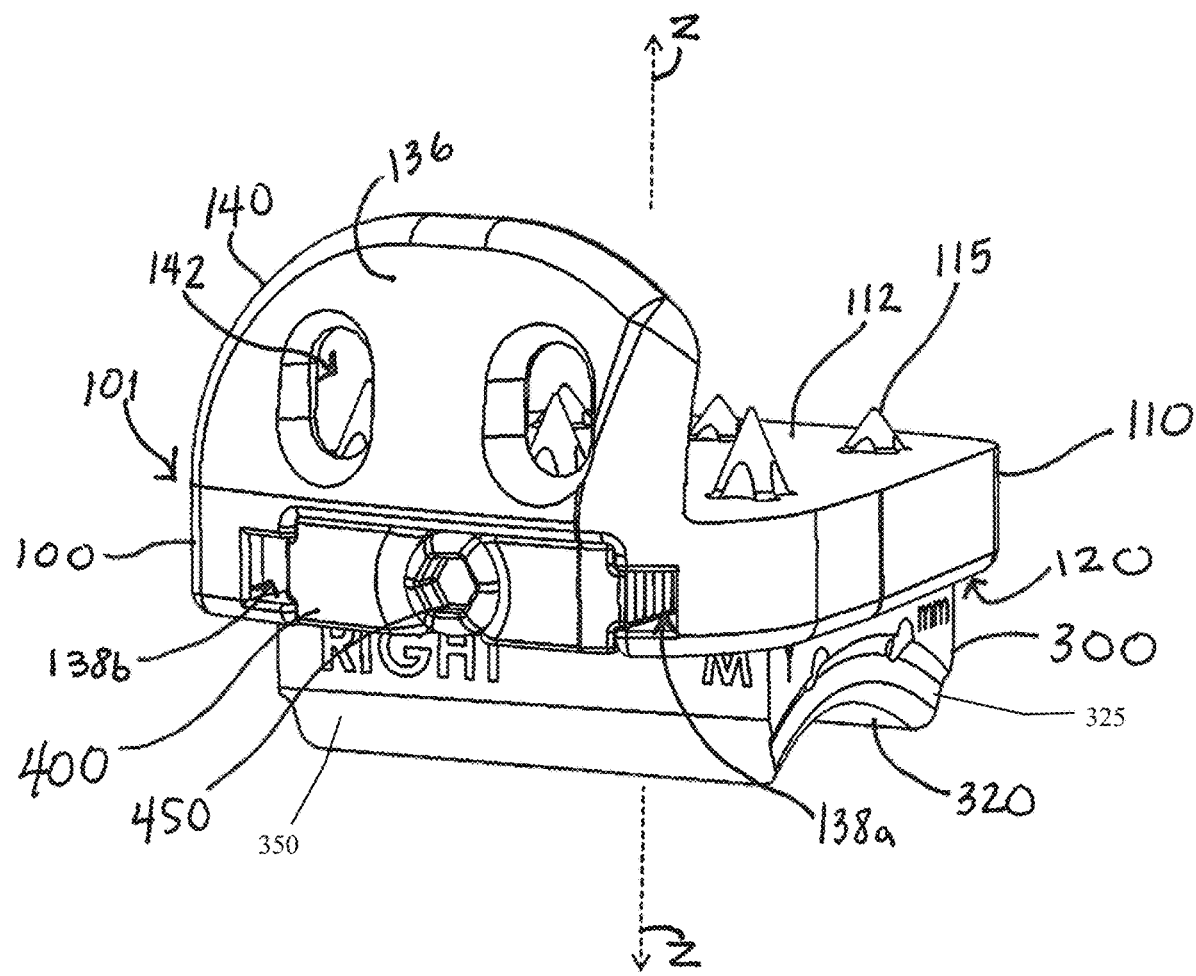
FIG. 2 illustrates an anterior, upper perspective view of a tibial implant coupled to an intermediate implant and an implant lock in accordance with the present disclosure.
Figure 3:
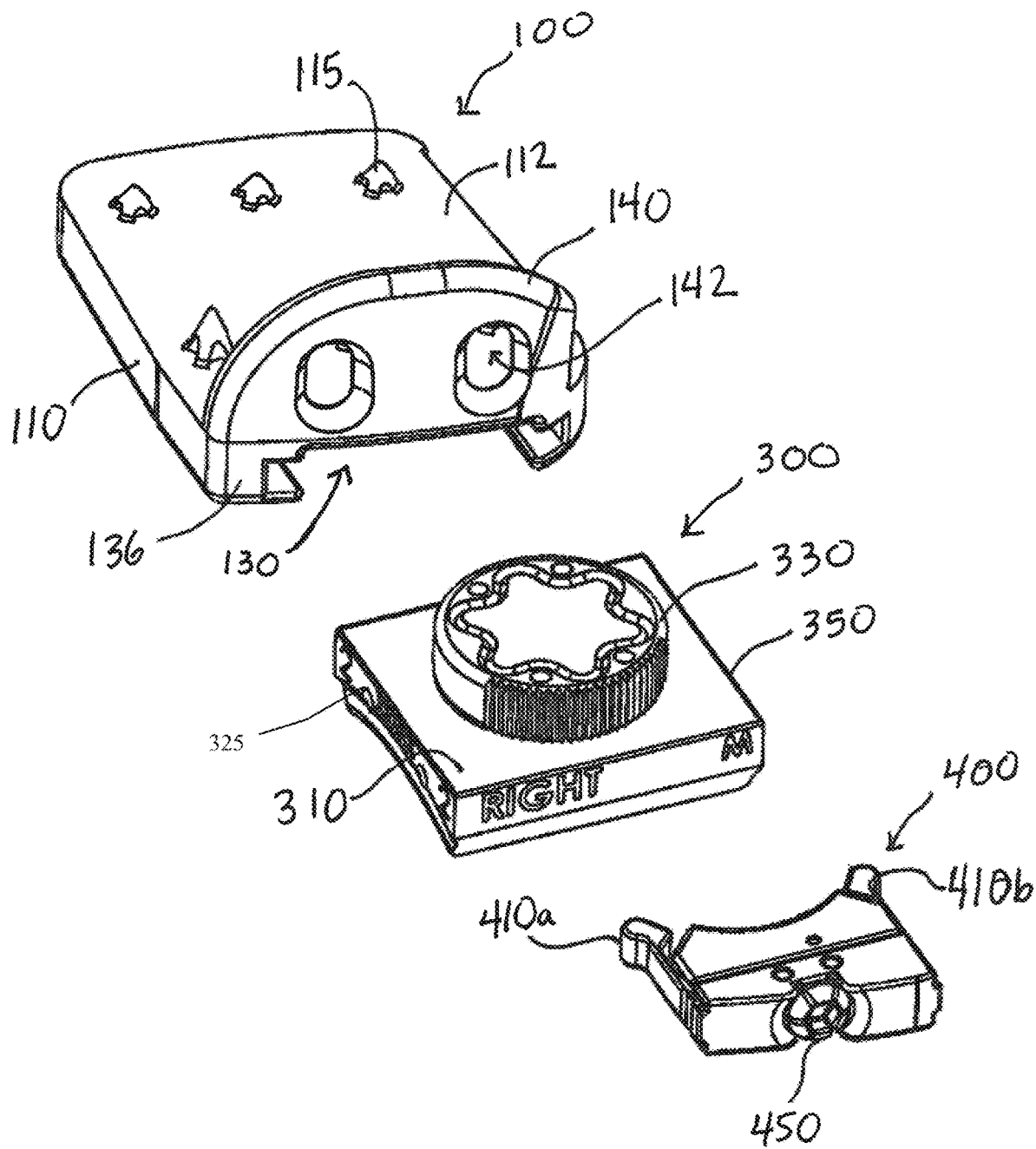
FIG. 3 illustrates an exploded view of the tibial implant, the intermediate implant and an implant lock in accordance with the present disclosure.
Figure 4A:
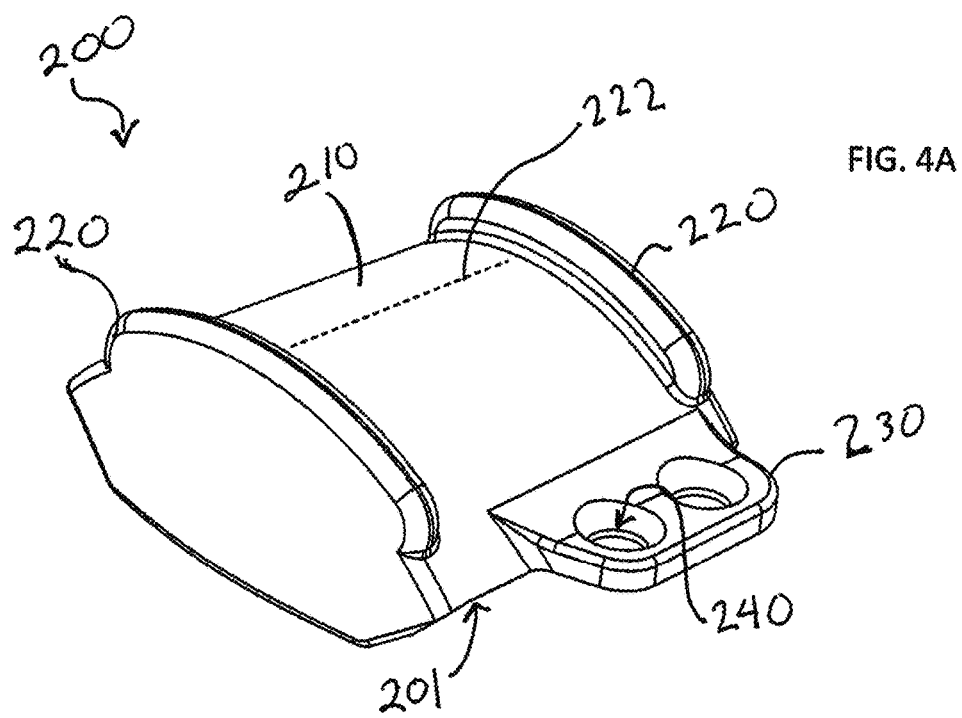
FIG. 4A illustrates a top perspective view of a talar implant in accordance with the present disclosure and FIG. 4B illustrates a bottom perspective view of the talar implant shown in FIG. 4A.
Figure 4B:
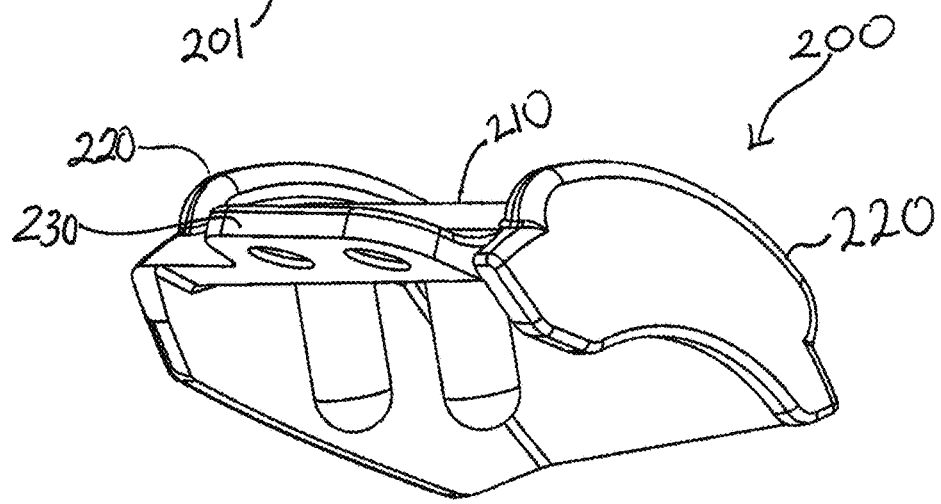

An embodiment of an ankle prosthesis according to the invention is illustrated in FIG. 1. Ankle prosthesis 10 includes a tibial implant 100, a talar implant 200, an intermediate implant 300, and an implant lock 400. The tibial implant 100 is configured to be implanted in or on the base of the tibia 30 of a patient. The talar implant 200 is configured to be implanted in or on the talus 20 of a patient. The intermediate implant 300 is configured to be disposed between the talar implant 200 and the tibial implant 100. The implant lock 400 is configured to fix the position (e.g., angular position) of the intermediate implant 300 relative to the tibial implant 100. FIG. 2 depicts an anterior, upper perspective view of the tibial implant 100 coupled to the intermediate implant 300 and the implant lock 400. FIG. 3 depicts an exploded view of the tibial implant 100, the intermediate implant 300, and the implant lock 400. FIG. 4A depicts an upper perspective view of the talar implant 200 and FIG. 4B depicts a bottom perspective view of the talar implant 200.

To facilitate the function of the prosthetic joint, the intermediate implant 300 and the talar implant 200 are configured to be moveable relative to each other along a contact interface 250 (FIG. 1) between a lower bearing surface 320 (FIG. 2) of the intermediate implant 300 and an upper bearing surface 210 (FIGS. 4A and 4B) of the talar implant 200. To this end, the lower bearing surface 320 of the intermediate implant is designed to bear against the upper bearing surface 210 of the talar implant 200 that is of complementary shape, so that the intermediate implant 300 can move by sliding relative to the talar implant 200 and vice versa. The talar implant upper surface 210 and intermediate implant lower surface 320 are rounded in shape, e.g., substantially spherical, cylindrical or frustoconical, so as to form a contact interface 250 (FIG. 1) that allows the foot to move in plantar flexion and in dorsal flexion relative to tibia 30 (FIG. 1).

Figure 5:
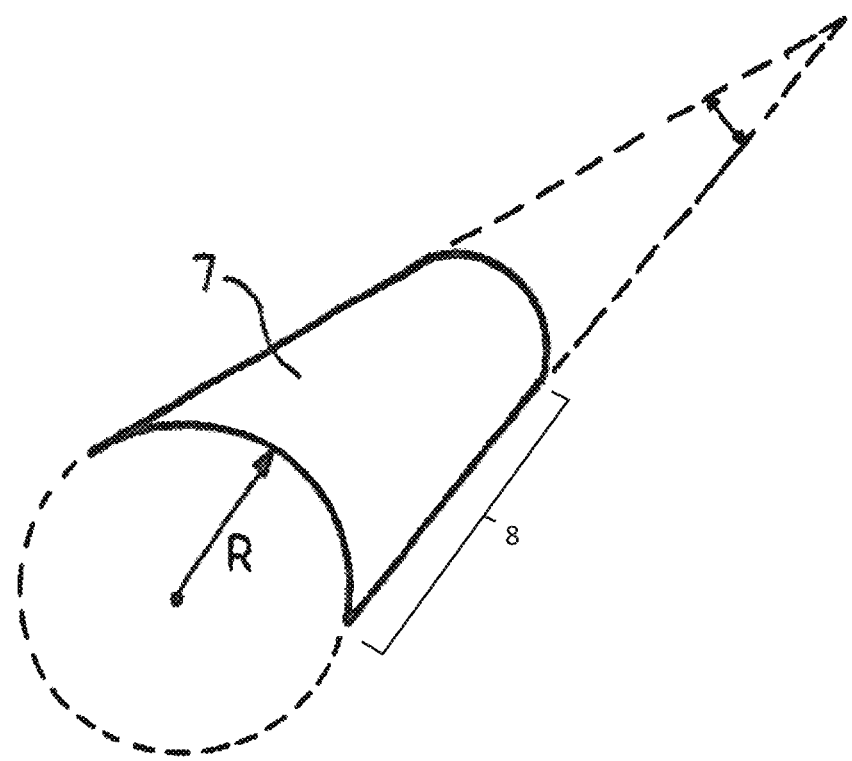
FIG. 5 illustrates a schematic of a frustoconical surface.

In the embodiment shown, the contact interface 250 between the intermediate implant 300 and the talar implant 200 can be considered as defining a surface that is a fraction of the surface of a substantially frustoconical shape (see FIG. 5 as an example of a fraction of the surface 7 of a substantially frustoconical shape 8). The contact interface 250 can be oriented such that its portion with larger radius R (FIG. 5) is directed substantially towards the outer side 45 of the ankle 15, i.e., away from the median axis of the body, when the prosthesis 10 is in place.

In the embodiment shown, the intermediate implant 300 comprises a concave lower surface 320, and the talar implant's upper surface 210, being complementary in shape and dimension to the lower surface 320, is convex. However, an inverse mechanical disposition is envisioned where the lower surface of the intermediate implant 300 is convex while the upper surface 210 of the talar implant 200 is concave.

In the embodiment shown, in order to restrain the lateral movement of the intermediate implant 300, the talar implant 200 can comprise rails 220, the pair of rails maintaining equal distance from each other along their length and each extending upwardly on a corresponding side of the upper surface 210. The rails 220 are spaced apart a distance that permits the lateral surface 325 of the intermediate implant base 350 to be disposed between the two rails. Because of the presence of rails 220, the intermediate implant 300 is guided by bearing on surface 320 against the rails during the movement of the talar implant 200 relative to the intermediate implant 300.

The talar implant 200 can be configured to be affixed to the talar bone. For example, the talar implant 200 can comprise an anterior plate 230 (FIGS. 4A and 4B). The anterior plate 230 projects outwardly (in a general posterior-to-anterior direction) from the anterior edge 201 of the talar implant 200. As shown in FIG. 1, the anterior plate 230 extends from the anterior edge 201 of the upper surface 210. The anterior plate 230 can contain one or more holes 240 (FIGS. 4A and 4B) to facilitate fixation with orthopaedic screws.

In the embodiment shown, with particular reference to FIGS. 2, 3, 6A, and 6B, the tibial implant 100 comprises a base 110 defining an upper surface 112 and an anterior shield 140. The upper surface 112 is configured to abut the end of the tibia 30. Anti-slip elements 115 can project outwardly from the upper surface 112 and are configured to maintain the alignment of the tibial implant 100 relative to the tibia 30. In an embodiment, the anti-slip elements 115 can be pointed and configured to penetrate bone. In the embodiment shown, the upper surface 112 is planar. Other anti-slip elements maybe also be considered suitable for use with the invention including elements extending upward past the sides of the tibia implant that can be secured to the sides thereof either through pressure or mechanical means including pins or screws.

The lower surface 120 of the tibial implant 100, which is viewable in FIGS. 6A and 6B, is configured to couple with the intermediate implant 300. At an interior region of the lower surface 120 is a recess 122. The recess 122 is configured to receive a portion of the intermediate implant, particularly, a projecting member 330. The recess 122 is configured to receive the projecting member 330. A sidewall 124 defines the perimeter of the recess. The recess 122 is shaped to permit the projecting member 330 to bear against the sidewall 124, and the sidewall 124 is configured to impede lateral movement of the projecting member 330. For example, the sidewall 124 extends vertically (e.g., extends in a plane that is parallel to the Z-Z axis) or may be angled or curved.

The recess 122 is sized and shaped to allow for rotation of the projecting member 330 within the recess 122. For example, the recess 122 can have a minimum transverse dimension (e.g., the width or the dimension along the Y-Y axis, shown in FIG. 6B) that is slightly more than the maximum transverse dimension of the projecting member 330, as discussed below. Also to facilitate rotation of the projecting member 330 within the recess 122, the sidewall 124 of the recess 122 can define a fraction of a circular shape.

The tibial implant 100 is also configured to couple with the implant lock 400 (FIGS. 1, 2, 3, and 10A to 10D). In the embodiment shown, tibial implant 100 comprises a slot 130 configured to receive at least a portion of the implant lock 400. Slot 130 is in communication with the recess 122 such that the implant lock 400 is able to couple directly with the projecting member 330 when the projecting member 330 is disposed within the recess 122. In the embodiment shown, slot 130 has a first end 131 and a second end 132. The first end 131 is closer to the recess 122 than the second end 132. An exposed surface of the tibial implant 100, such as anterior face 136, defines the second end 132.

The tibial implant 100 can be configured such that the implant lock 400 is inserted into the slot 130 at a direction that is substantially perpendicular to the Z-Z axis (e.g., the axis of rotation of the projecting member 330). For example, the slot 130 extends within a plane through which the recess 122 also extends, and such plane can be substantially perpendicular to the Z-Z axis (e.g., the axis of rotation of the projecting member 330). In embodiments, substantially perpendicular can be within 10°, 5°, 3°, 2°, or 1° of the perpendicular. Implant lock 400 is configured to be inserted into slot 130. In order to facilitate insertion, the height (e.g. dimension along the Z-Z axis shown in FIG. 2) of the implant lock 400 can be of a dimension which is smaller than the height of slot 130.

The implant lock 400 and the tibial implant 100 can be configured to interlock with each other. When interlocked, movement of the implant lock 400 relative to the tibial implant 100 is constrained. For example, in the embodiment shown, the sidewall 134 defining the slot comprises two notches 136a, 136b. The notches 136a, 136b can be located on opposing sidewall surfaces such that they face each other. Each notch 136a, 136b is configured to receive and interlock with a projection 410a, 410b of the implant lock 400 (FIG. 10A to 10D). The implant lock 400 can be configured such that the projections 410a, 410b are pushed or snapped into interlocking engagement with the notches 136a and 136b.

Figure 7:
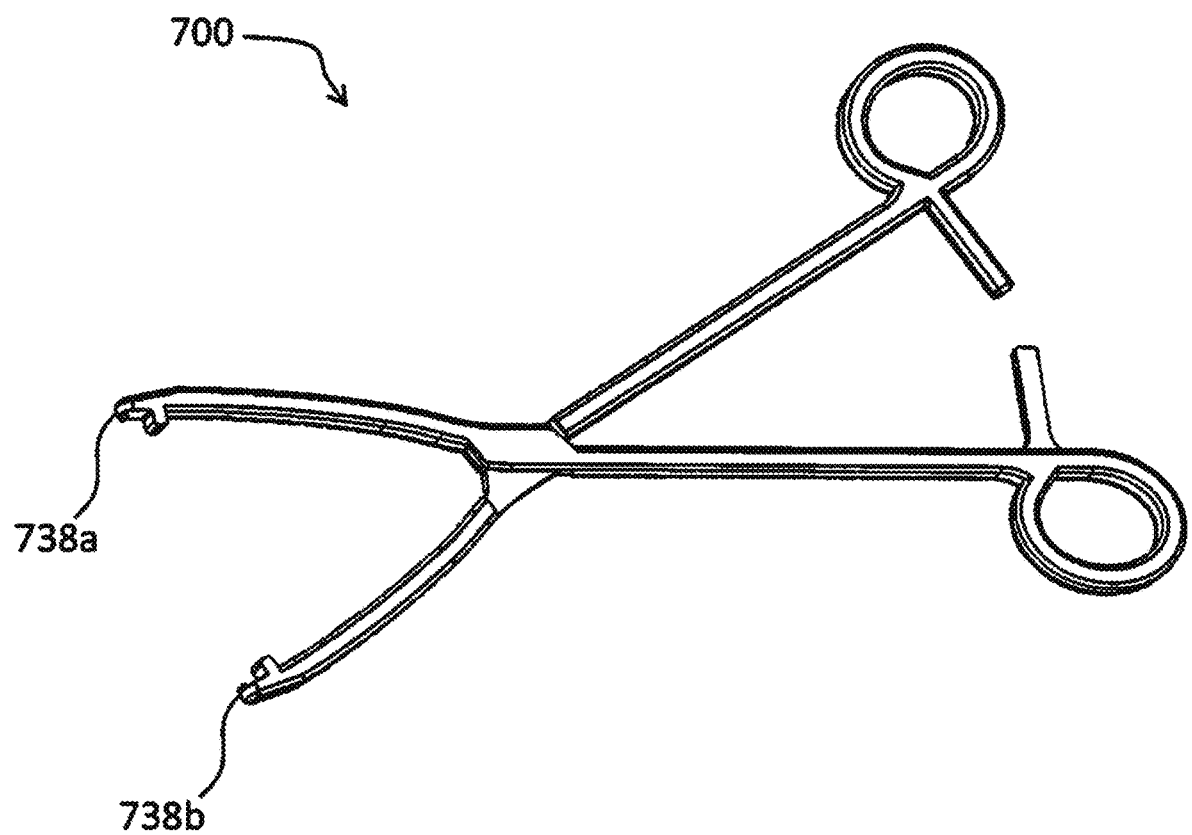
FIG. 7 illustrates a grasper which can be used for removal of the implant lock shown in FIG. 2.

The slot 130 and the implant lock 400 can be configured such that the implant lock 400 is retrievable from the slot 130. A tool, for example a surgical grasper commonly used during surgery, can be used to retrieve the implant lock. FIG. 7 shows an example of such a grasper that can be used as grasper 700. To facilitate retrieval, slot 130 has an overall width (e.g., dimension along the Y-Y axis shown in FIG. 6B) which is greater than the width of the implant lock 400. This width at the second end 132 is sufficient to provide some space 138a, 138b on both sides of the implant lock 400. This space 138a and 138b (FIG. 2) permits the nose portions 738a and 738b of grasper 700 to be inserted into the slot 130 on both lateral sides 405a, 405b of the implant lock 400 in order to pull and retrieve the implant lock 400. The lateral sides 405a, 405b of the implant lock 400 can each comprise surface contours 437 configured to interlock with the retrieval tool. Similarly, a roughened surface on lateral sides 405a, 405b and nose portions 738a, 738b can provide sufficient coupling force to facilitate removal of implant lock 400.

The tibial implant 100 is likewise provided with an anterior shield 140 configured to resist the tibial implant 100 from migrating posteriorly. The anterior shield 140 projects upwardly from the anterior edge 101 of the implant 100. When said implant is in place in the patient, the anterior shield 140 would extend upwards along the tibia bone 30. Thus, as shown in FIG. 1, the anterior shield 140 extends from the anterior edge 101 of the implant 100 upward and obliquely relative to upper surface 112. The anterior shield 140 can define one or more holes 142 for inserting one or more screws to facilitate fixing the implant to the tibia bone.

The tibial implant 100 and the talar implant 200 can be made of a biocompatible metal alloy, such as cobalt chromium alloy, titanium alloy, stainless steel or any other material that is comparably able to withstand the forces in and around the ankle joint as well as being physiologically tolerated.

In some embodiments, the tibial implant 100 and/or the talar implant 200 can comprise a coating of one or more layers on the surface intended to be in contact and adhere to bone. Such coatings can facilitate bone apposition, osteointegration and/or osteoinduction. In some embodiments, a coating of plasma-sprayed titanium is applied to the talar implant 200 and/or the tibial implant 100 on the surfaces in contact with bone to promote bone apposition and osteointegration. The plasma-sprayed titanium coating can comprise an average thickness between 100 to 800 µm, such as 200 to 300 µm. In some embodiments, a coating of calcium phosphate, such as hydroxyapatite, is applied to the talar implant 200 and/or the tibial implant 100 on the surfaces in contact with bone to promote bone apposition, osteointegration and/or osteoinduction. The calcium phosphate coating can comprise an average thickness between 25 to 200 µm, such as 60 to 100 µm. In some embodiments, a dual coating of plasma-sprayed titanium, followed by a coating of calcium phosphate is applied to the talar and/or the tibial implant. The dual coating can comprise an average thickness between 125 and 1000 µm, such as 260 to 400 µm. A tibial implant 100 and/or the talar implant 200 can comprise a titanium coating, a calcium phosphate coating, or both.

With particular reference to FIGS. 2, 3, and 8A, 8B, and 8C, the intermediate implant 300 comprises a base 350 and the projecting member 330. The base 350 defines an upper surface 310 and the curved lower surface 320 opposite the upper surface 310, and the projecting member 330 extends outwardly from the upper surface 310. The intermediate implant 300 can be in frictional contact with the tibial implant 100 and talar implant 200 at the upper surface 310 and the lower, curved surface 320, respectively.

The projecting member 330 is configured to extend into the recess 122 of the tibial implant 100 and to rotate relative to the tibial implant 100. In particular, the projecting member 330 is sized to rotate within the recess 122. As mentioned above, the projecting member 330 is sized to have a maximum transverse dimension that is slightly less than the minimum transverse dimension of the recess 122. In embodiments, the maximum transverse dimension of the projecting member 330 can be at least 0.1%, 0.2%, 0.3%, 0.4%, 0.5%, 1%, 1.5%, or 2% less than the minimum transverse dimension of the recess 122. In some embodiments, the projecting member 330 can rotate at least 70 degrees, at least 180 degrees, or 360 degrees relative to the tibial implant 100 when disposed in the recess 122. In some embodiments, the projecting member 330 can freely rotate relative to the tibial implant 100 when disposed in the recess 122.

The projecting member 330 can have a transverse cross-sectional shape that facilitates load distribution along the lateral surface 335 of the projecting member 330 as it bears against the sidewall of the recess 122. For example, the transverse cross-section of the projecting member 330 can define a rounded shape, such as a substantially circular shape. However, the transverse cross-sectional shape of the projecting member 330 can be any shape such as a square, pentagon, star, or other regular or irregular, convex or non-convex polygonal shape.

The projecting member 330 is configured to interlock with a portion of the implant lock 400, such as the first end 402 of the implant lock 400. For example, in the embodiment shown, the projecting member 330 comprises a lateral surface 335 having one or more interlocking surface features, such as cogs 337, which are configured to interlock with corresponding cog(s) 412 on the first end 402 of the lock 400.

The projecting member 330 can be configured to have a lateral surface 335 that is more wear resistant than the lower surface 320. For example, the projecting member 330 or a portion thereof defining the lateral surface 335 can comprise a material that is tougher, harder, and/or of a higher modulus than the material of the intermediate implant 300 that defines the lower surface 320. In the embodiment shown, the projecting member 330 comprises an inner core 332 of a first material and a circumscribing member 334 of a second material, wherein the second material is tougher, harder, and/or of a higher modulus than the first material. In some embodiments, the circumscribing member 334 can be made of a biocompatible metal alloy, such as titanium alloy, cobalt chromium alloy or stainless steel, or any other material that is tougher, harder, and/or of a higher modulus than the material used for the intermediate implant 300. The portion of the intermediate implant 300 defining the lower surface 320 can be made of polyethylene, polytetrafluoroethylene, polyether-ether-ketone, nylon, copolymers or composites thereof, or other suitable material which can withstand the forces of and about the ankle joint and provide relatively low friction contact with the talar implant 200.

Moreover, the circumscribing member 334 can be configured so that it is coupled in fixed relation to the remainder of the intermediate implant 300. For example, the inner core 332 and the circumscribing member 334 are coupled so that the circumscribing member 334 resists rotation relative to the inner core 332 (see FIGS. 8A and 8C.) In some embodiments, the inner core 332 has a non-circular, transverse cross-sectional shape and the circumscribing member 334 defines an interior opening that has a transverse cross-sectional shape that is the same as the transverse cross-sectional shape of the inner core 332. In the embodiment shown, the transverse cross-sectional shape is a polygonal shape. Alternatively, or in addition thereto, the circumscribing member 334 can be configured to couple in fixed relation to the base 350 of the intermediate implant 300. For example, the circumscribing member 334 can interlock with the base 350, such as through one or more mortise-tenon structures 360.

The transverse dimension of the projecting member 330 can be any suitable size. In some embodiments, the transverse dimension of the projecting member 330 is the same as or less than that of the base 35. In some embodiments, the maximum transverse dimension of the projecting member 330 can be between 20% and 85% of the maximum transverse dimension of the base 350 of the intermediate implant, such as between 30% to 80% or 40% to 80% or 50% to 80%.

Figure 9A:
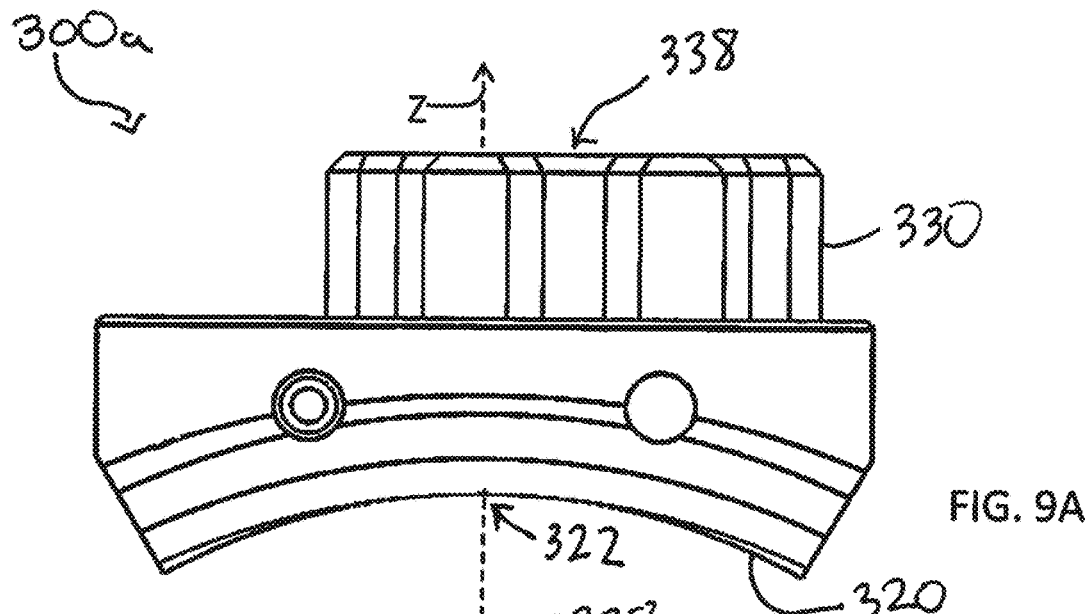
FIG. 9A illustrates a right side view of an embodiment of an intermediate implant with a posterior alignment.
Figure 9B:
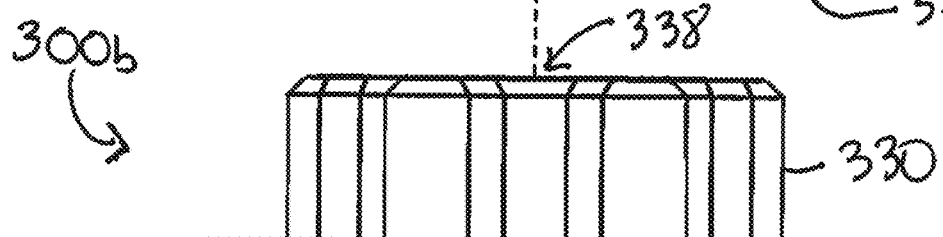
FIG. 9B illustrates a right side view an embodiment of an intermediate implant with a neutral alignment.
Figure 9C:
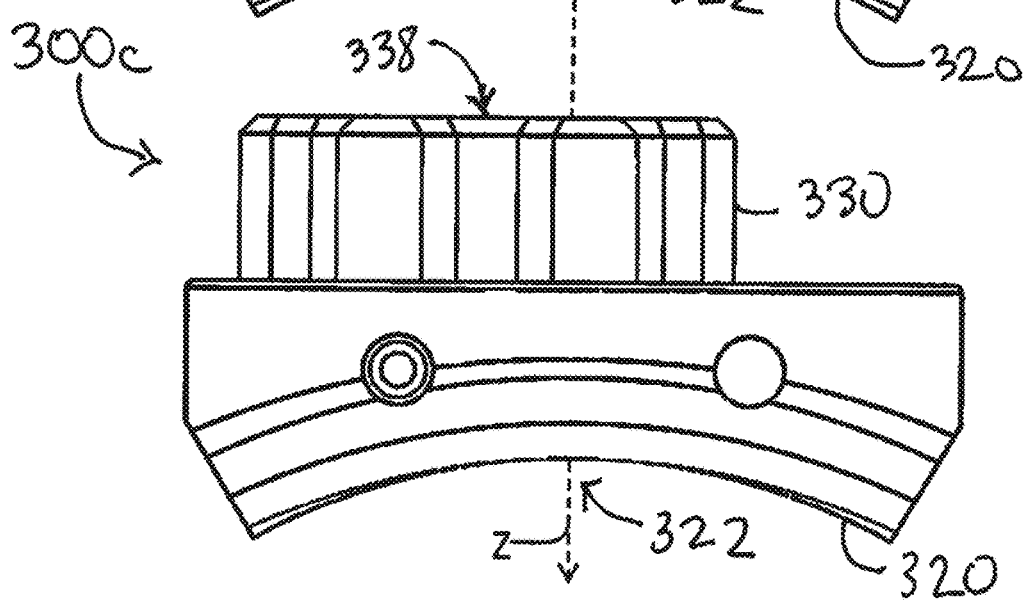
FIG. 9C illustrates a right side view an embodiment of an intermediate implant with an anterior alignment.
Figure 10A:
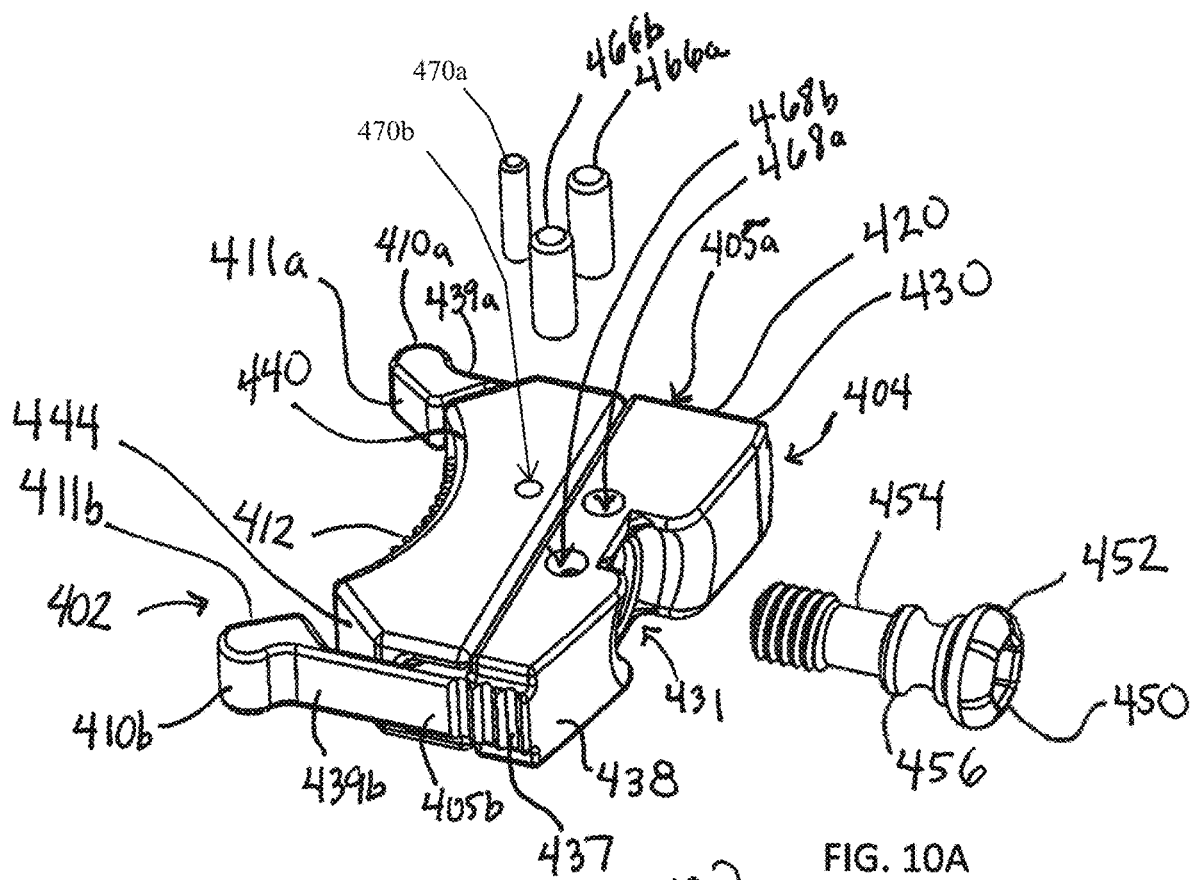
FIG. 10A illustrates an exploded view of the implant lock shown in FIG. 2.
Figure 10B:
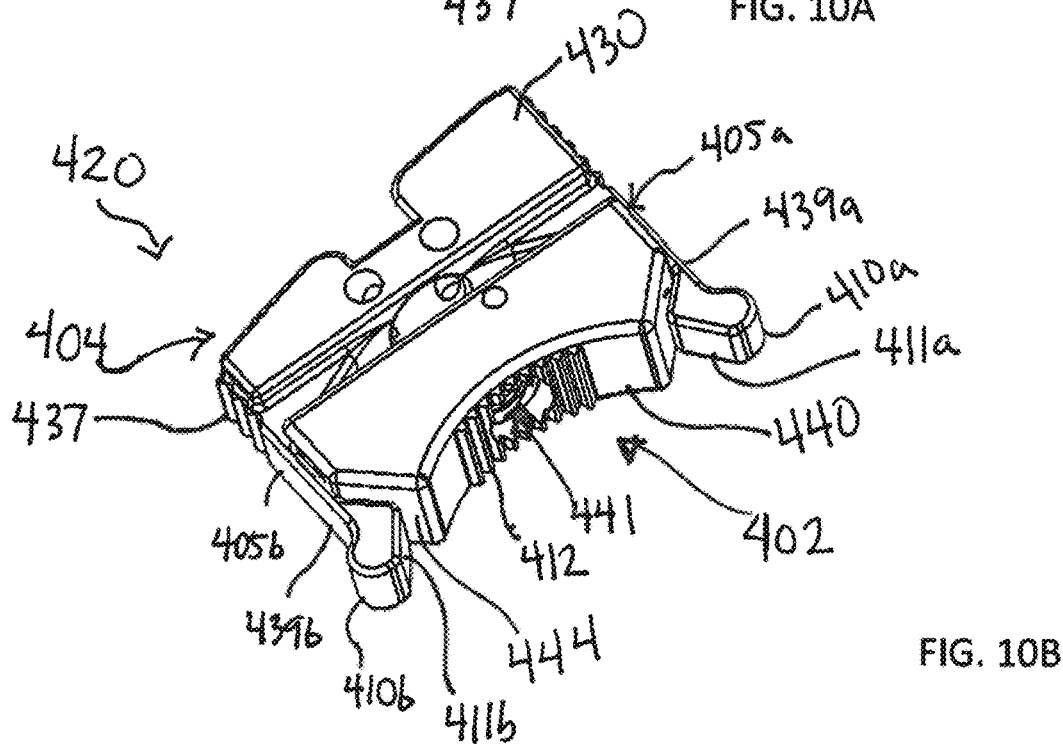
FIG. 10B illustrates a lower, perspective view of the implant lock shown in FIG. 10A.
Figure 10C:
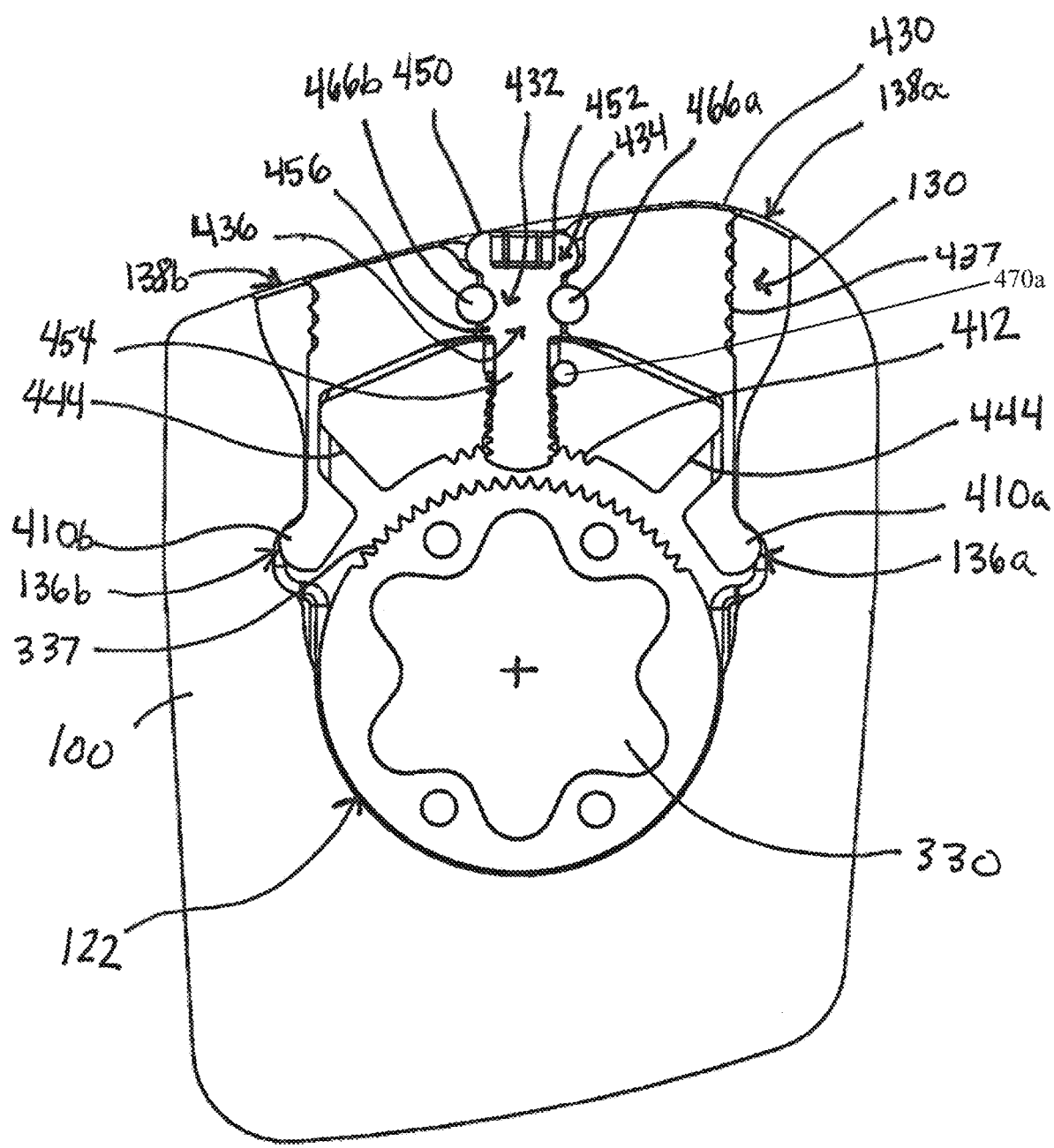
FIGS. 10C and 10D illustrate a cross-sectional view of the implant lock and the tibial implant shown in FIG. 2.
Figure 10D:
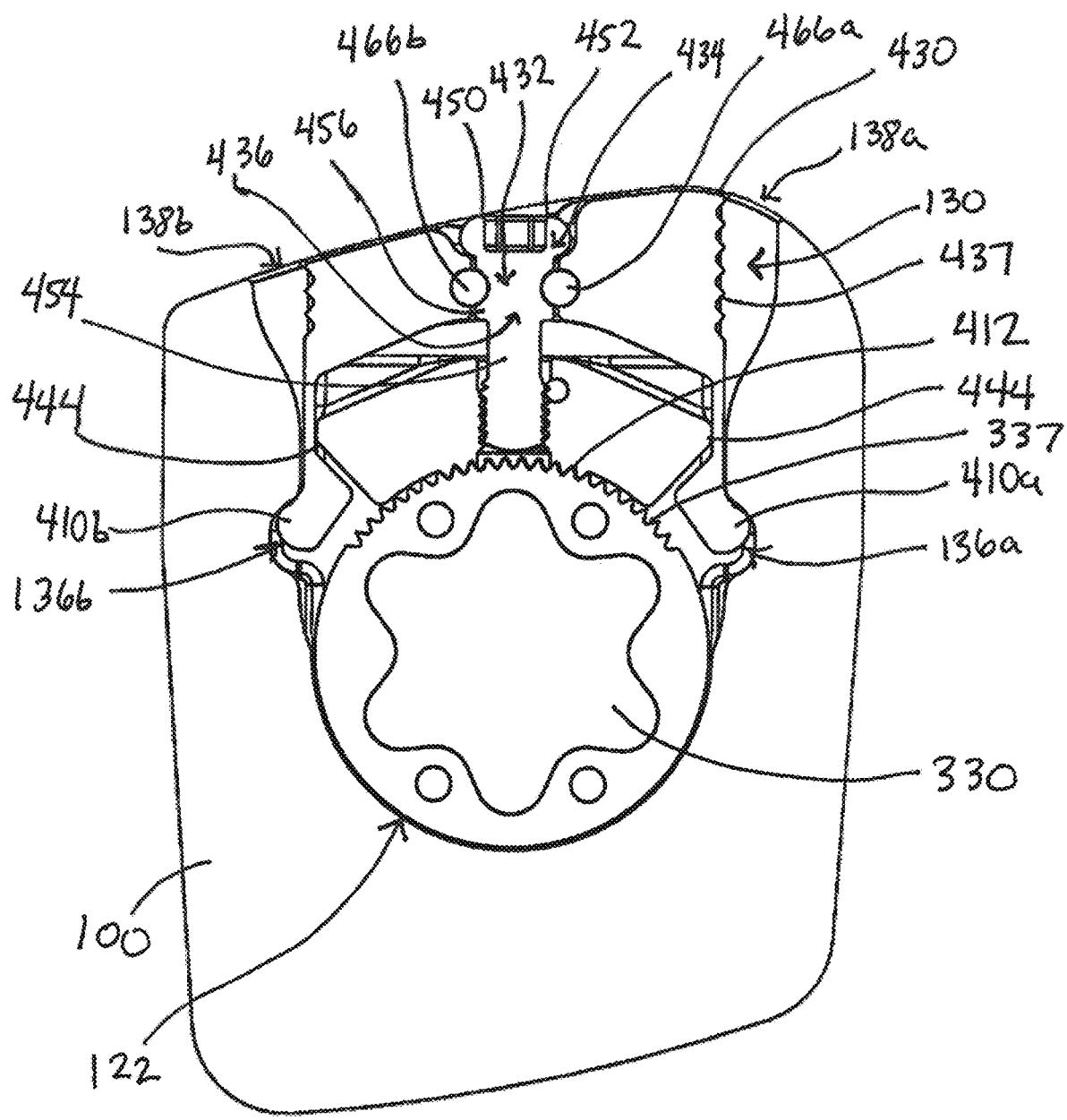

To facilitate obtaining an ankle prosthesis that has an alignment which is closer to the specific anatomy of the patient, an ankle prosthesis kit or an intermediate implant replacement kit can comprise a plurality of intermediate implants 300 that provide different configurations to allow varied alignment of the lower, curved surface 320 relative to the tibial implant 100. In particular, variance of alignment can be effected by the position of the projecting member 330 relative to the apex 322 of the lower curved surface 320. FIGS. 9A, 9B and 9C show three variations in alignment of the projecting member 330 relative to the apex 322 of the lower curved surface 320. The three variations shown in the figures comprise a shift in the position of the projecting member 330 only along an anterior-posterior axis. A first intermediate implant 300a of the kit can be configured such that a center 338 of the projecting member 330 be posterior to the apex 322. (FIG. 9A illustrates an embodiment of the first intermediate implant 300a.) A second intermediate implant 300b of the kit can be configured such that a center 338 of the projecting member 330 be disposed directly above (e.g., vertically aligned or substantially aligned along an axis that is parallel with the Z-Z axis) the apex 322. (FIG. 9B illustrates an embodiment of the second intermediate implant 300b.) A third intermediate implant 300c of the kit 50 can be configured such that a center 338 of the projecting member 330 be anterior to the apex 322. (FIG. 9C illustrates an embodiment of the first intermediate implant 300c.). The amount of anterior or posterior offset, A, from the apex 322 would be dependent upon the size of the tibial implant 100. In particular the offset would be a fraction of the anterior-posterior length dimension of the tibial implant and can be between 2 to 10% of the anterior-posterior length, such as 2, 3, 4, 5, 6, 7, 8, 9, or 10%.

To facilitate obtaining an ankle prosthesis that has an alignment which is closer to the specific anatomy of the patient, the intermediate implant 300 can be configured such that the position of the projecting member 330 on the upper surface of the intermediate implant is adjustable. (Embodiment not illustrated.) For example, a plurality of fastening points (e.g., mortise structures) can be provided on the upper surface of the intermediate implant to which the projecting member 330 can be coupled. A clinician can select which fastening points to which the projecting member 330 should be coupled based on the patient's anatomy.

Another factor influencing fit of the ankle prosthesis is the thickness (or height) of the intermediate implant 300, particularly the base 350. To account for this variation amongst patients, an ankle prosthesis kit or an intermediate implant replacement kit can comprise a plurality of intermediate implants 300 that have different thicknesses. The thickness can be between 5 and 12 mm at the thinnest cross sectional point of the base 350, such as 5, 6, 7, 8, 9, 10, 11, or 12 mm.

With particular reference to FIGS. 2, 3, and 10A to 10D, the implant lock 400 is configured to resist rotation of the projecting member 330 relative to the tibial implant 100 by applying a force to the projecting member that is only substantially perpendicular to the axis of rotation of the projecting member 330 (e.g., substantially perpendicular to the Z-Z axis). (In embodiments, substantially perpendicular can be within 10°, 5°, 3°, 2°, or 1° of the perpendicular.) The implant lock 400 can also be configured to interlock with the tibial implant 100. The interlocking can be releasable.

In the embodiment shown, the implant lock 400 comprises an insert or main body portion 420, which is formed from two sub-portions, namely a head portion 430 and a tail portion 440. When inserted into the slot 130, the tail portion 440 would be closer to the projecting member 330 than the head portion 430.

These two portions 430 and 440 are configured to move relative to each other along an axis that is generally perpendicular to the axis of rotation of the projecting member 330 or that passes through the first end 402 and the second end 404 of the implant lock 400. In the embodiment shown, the implant lock 400 further comprises a screw 450 and is configured such that the head portion 430 and the tail portion 440 move away from each other as the screw 450 is rotated in a first direction and move toward each other as the screw 450 is rotated in a second direction. In particular, each of the head portion 430 and the tail portion 440 comprise a through-bore 431 and 441, respectively, through which the screw 450 can extend. Through-bore 441 of the tail portion 440 is threaded. The through-bore 431 of the head portion 430 is not threaded, and the screw 450 is able to freely rotate within the through-bore 431

In addition, head portion 430 and screw 450 are configured such that the axial position of the screw 450 relative to the head portion 430 does not change as the screw 450 is rotated. For example, in the embodiment shown, screw 450 comprises a head 452 coupled to a shaft 454 and a collar 456 spaced apart from the head 452 and circumscribing the shaft 454. The through-bore 431 of the head portion 430 has a transverse dimension that is narrower at an intermediate section 432 than at the end sections 434 and 436. The section of the shaft 454 that is disposed within the narrower, intermediate section 432 of through-bore 431 is the section between the collar 456 and the head 452. In the embodiment shown, this narrower intermediate section 432 can be formed by two retaining pins 466a, 466b pressed into holes 468a, 468b intersecting through-bore 431 and capturing the shaft 454 above the collar 456. As the screw 450 is rotated, the collar 456 or the head 452 of the screw 450 bears against the retaining pins 466a, 466b. This facilitates the movement of the tail portion 440 away from the head portion 430.

Head portion 430 can also be configured to interlock with the tibial implant 100. For example, in the embodiment shown, head portion 430 comprises a body 438 coupled to two legs 439a, 439b projecting from the body 438 such that the legs 439a, 439b flank the tail portion 440. Each leg 439a, 439b comprises two projections, a first projection 410a, 410b facing outward and a second projection 411a, 411b facing inward. The tail portion 440 tapers such that it has a wider transverse dimension nearer the head portion 430. The tapering of the tail portion 440 facilitates the sidewall 444 of the tail portion 440 to bear against the inward facing, second projection 411a, 411b and press projections 410a, 410b into the respective notch 136a, 136b in the sidewall 134 defining the slot 130.

By rotating the screw 450 in a first direction, such as to partially withdraw it from the through-bore 441 of the tail portion 440, the tail portion 440 moves away from the head portion 430 and toward the recess 122 or toward the projecting member 330 disposed within the recess 122. This motion facilitates the tail portion 440 interlocking with the projecting member 330, such as by the cog(s) 412 of the tail portion 440 interlocking with cogs 337 of the projecting member 330 (see FIG. 10D). This motion can also facilitate the head portion 430 interlocking with the tibial implant 100 through the wedge surface interface of sidewall 444 with second projections 411a and 411b.

Implant lock 400 can further be configured to bind the screw 450 such that rotation of the screw 450 is impeded when locking the implant lock 400. For example, to facilitate impeding rotation of the screw 450 when locking, in the embodiment shown, implant lock 400 can further comprise an abutment pin 470a and a hole 470b intersecting through-bore 441 of the tail portion 440. As screw 450 is rotated, such as to partially advance it into the through-bore 441 of the tail portion 440, the threads of the screw 450 will abut the pin 470a, thereby binding the screw by galling and impeding its rotation.

By rotating the screw 450 in a second direction, such as to advance it into the through-bore 441 of the tail portion 440, the tail portion 440 moves toward the head portion 430 and away from the recess 122 or away from the projecting member 330 disposed within the recess 122. This motion facilitates the tail portion 440 unlocking with the projecting member 330, such as by the cog(s) 412 of the tail portion 440 releasing or decoupling from the cogs 337 of the projecting member 330 (see FIG. 10C). This motion can also facilitate the head portion 430 unlocking with the tibial implant 100 through the freeing of the wedge surface interface of sidewall 444 with second projections 411a and 411b retracting from the respective notches 136a, 136b in the sidewall 134.

As mentioned above, there can be different configurations of the intermediate implant 300 that provide different degrees of alignment of the lower, curved surface 320 relative to the tibial implant 100. When a particular configuration of the intermediate implant 300 is inserted in vivo, its curvature on the lower surface 320 will align with that of the upper surface 210 of the talar implant 200. Whether or not this particular configuration is optimal as compared to the other options, with reference to FIGS. 11A to 11D, a measurement tool assembly 600 can be used to indicate where the projecting member 330 is within the recess 122 or the slot 130, whether it is anterior, posterior, or generally in alignment with the apex 222 of upper surface 210 of the talar implant 200. The measurement tool assembly 600 comprises a bar 610 that is sized to extend through the slot 130 and the recess 122 and a trial intermediate member 620. In the embodiment shown, the bar 610 defines a hole 615 configured to receive a trial projecting member 650 coupled to and extending from base 660. The bar 610 also comprises marking 630 which indicated the distance from the hole 615, thereby indicating the relative anterior position of the apex 222 of upper surface 210 talar implant 200 to that of the anterior face 136 of tibia implant 100. The markings 630 can comprise numerical values and/or can comprise symbols or colors which represent the numerical vales.

Figure 11A:
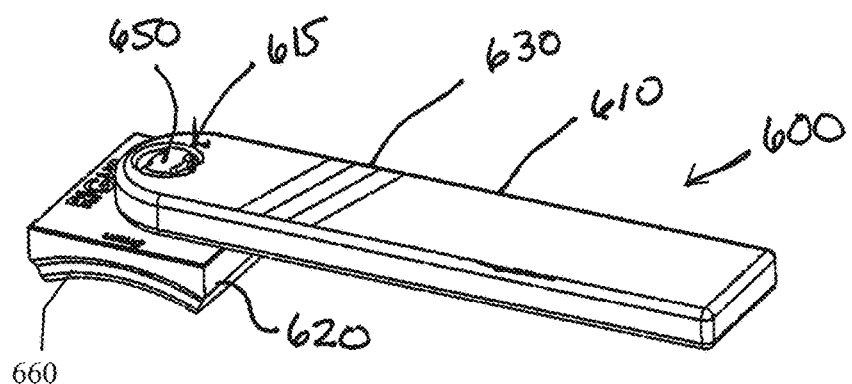
FIG. 11A illustrates an upper perspective view of an embodiment of a measurement tool in accordance with the present disclosure.
Figure 11B:
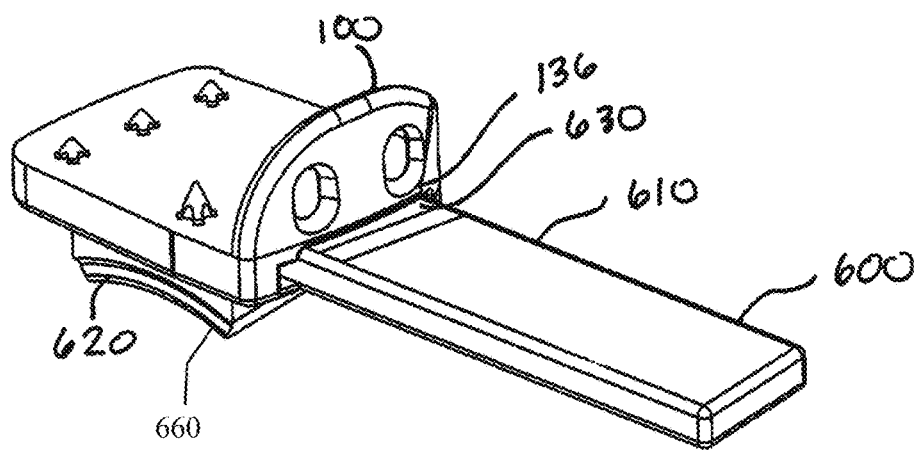
FIGS. 11B to 11D illustrate an upper perspective view of a measurement tool measuring the alignment of the intermediate implant with respect to the tibial implant in accordance with the present disclosure.
Figure 11C:
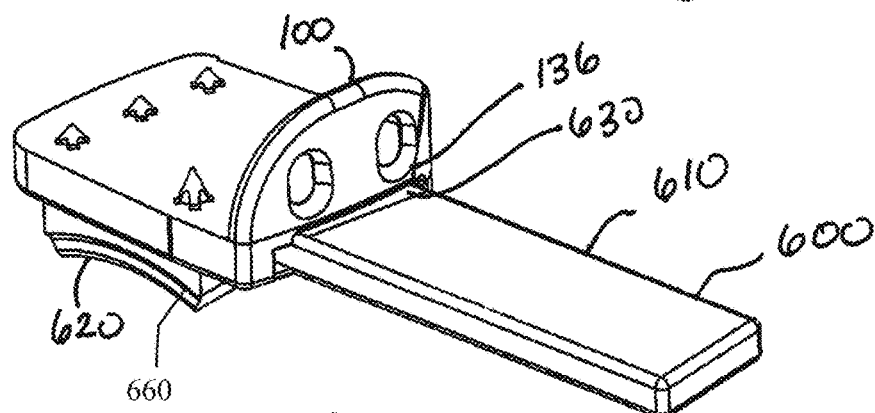
Figure 11D:
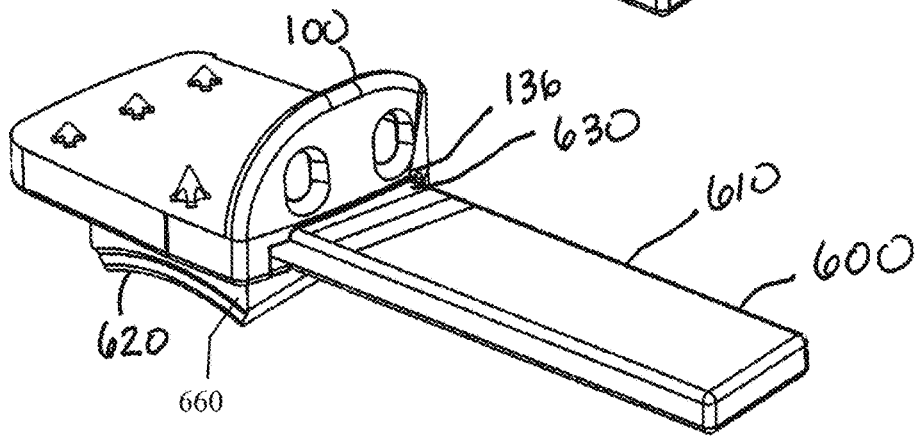
Figure 12A:
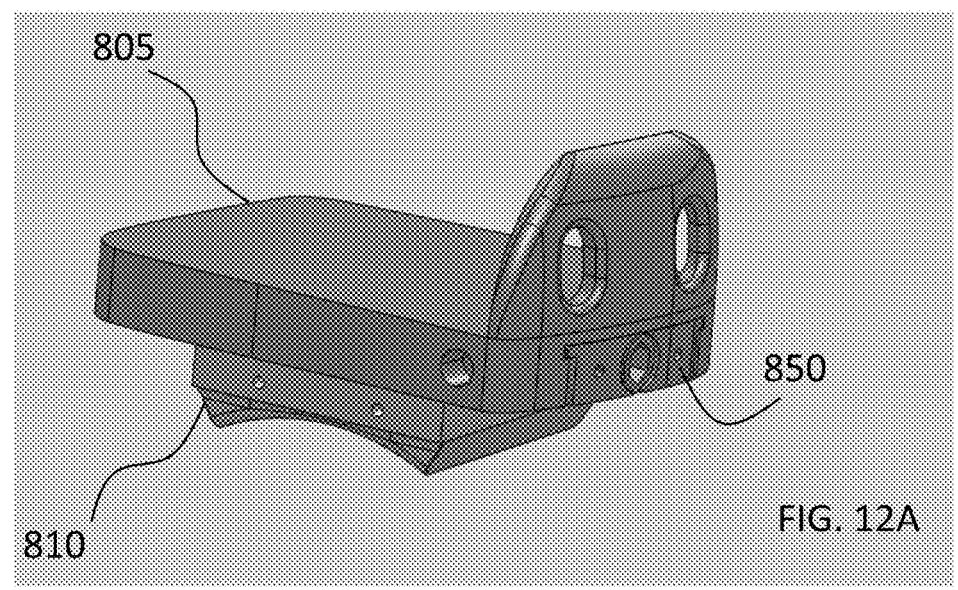
FIGS. 12A to 12D illustrates another embodiment of a tibial implant and an intermediate implant of an ankle prosthesis.
Figure 12B:
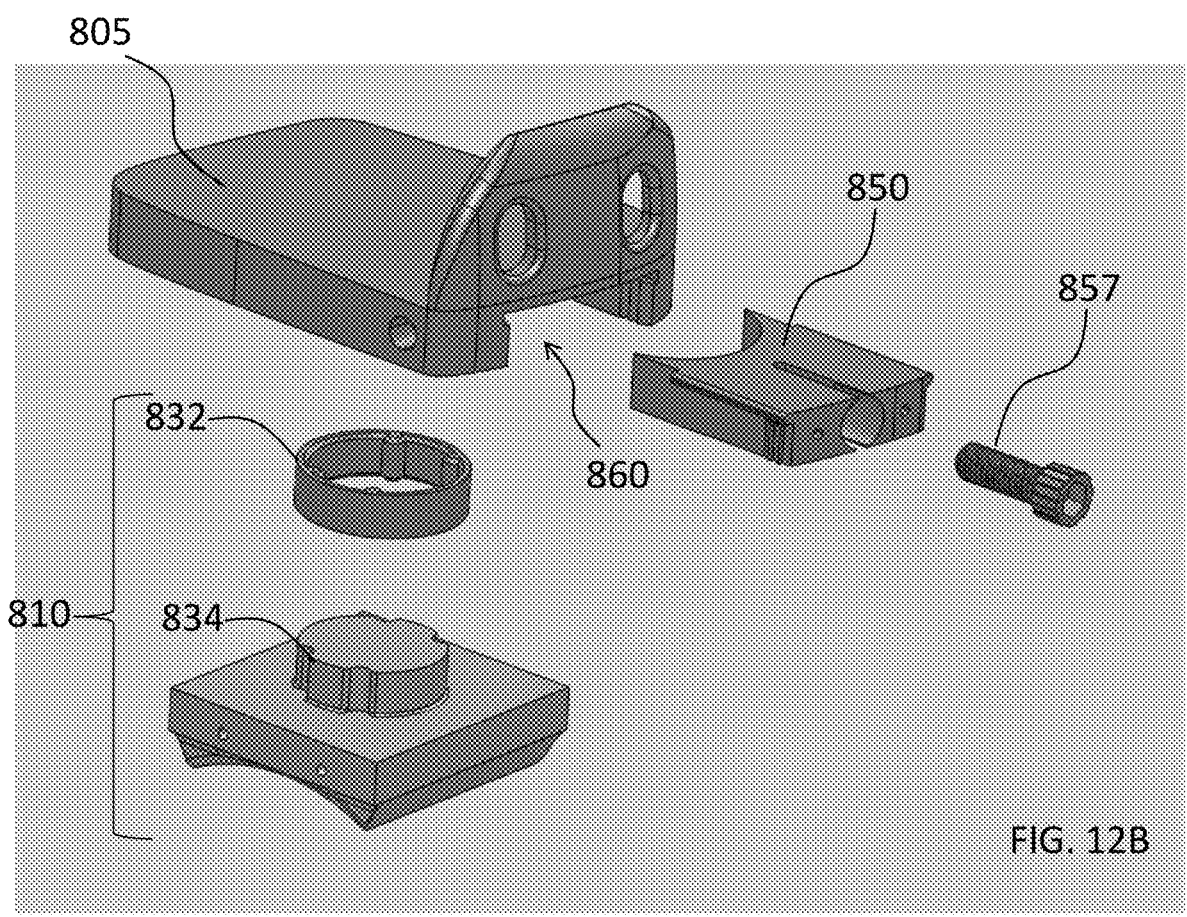
Figure 12C:
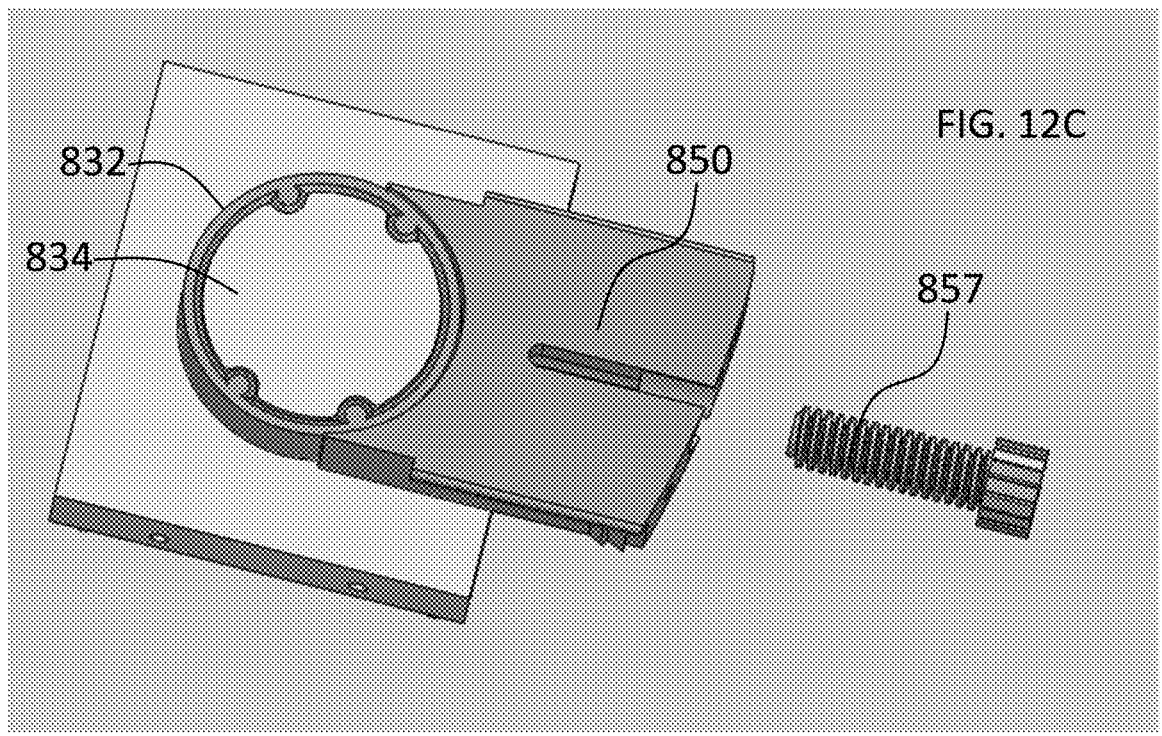
Figure 12D:
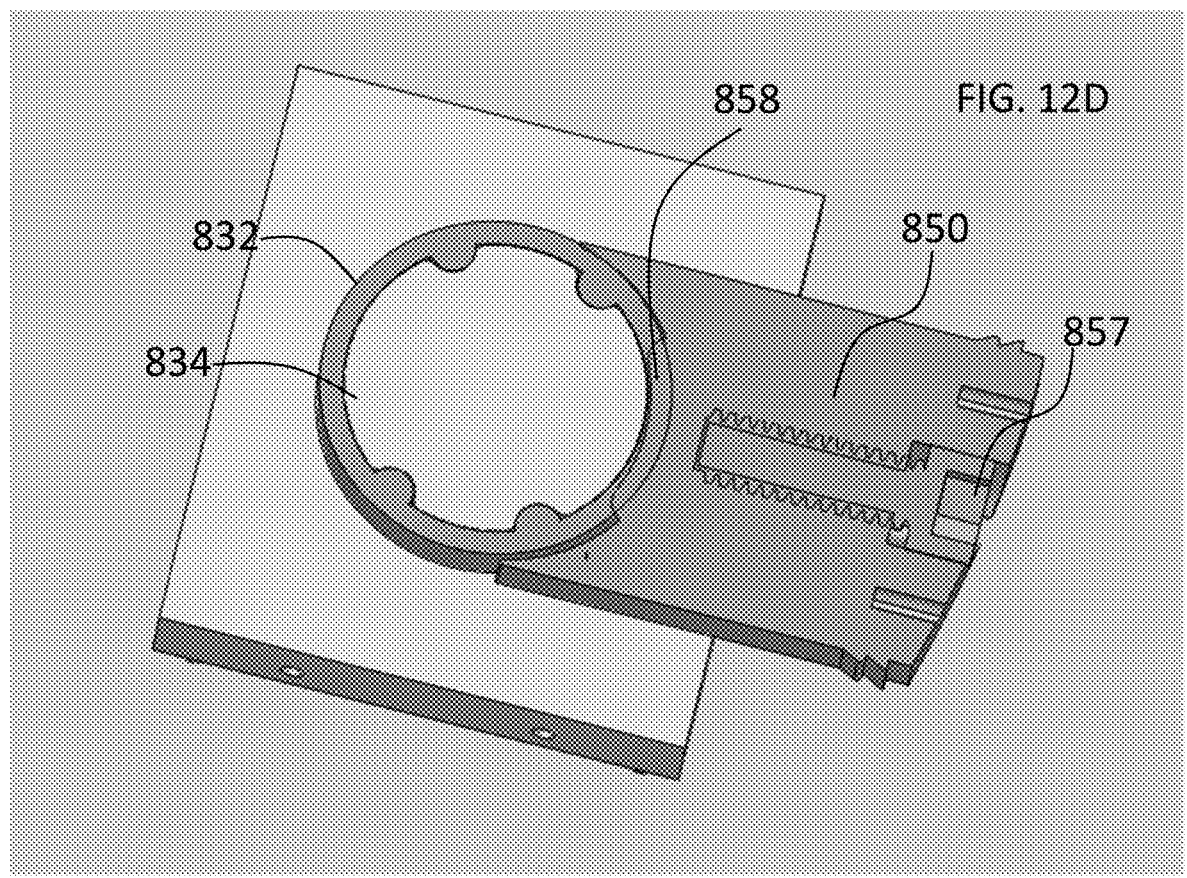

To use the measurement tool assembly 600, a trial intermediate implant 620 is assembled to bar 610, such as by disposing the trial projecting member 650 of the trial intermediate implant 620 in the hole 615. The trial projecting member 650 with the bar 610 coupled thereto is inserted into position between the tibial implant 100 and talar implant 200 such that the trial projecting member 650 and the bar 610 are disposed within the recess 122 and slot 130. The marking 630 that is visible at the anterior face 136 of the tibial implant 100 is indicative of whether the trial intermediate implant 620 is generally in neutral alignment (FIG. 11B), posterior (FIG. 11C), or anterior (FIG. 11D).

An embodiment of the trial intermediate implant 620 can be the same as embodiments of the intermediate implant 300 described above except that the trial projecting member 650 has smaller transverse dimensions than that of the intermediate implant 300 and the trial projecting member 650 is configured to assemble to the bar 610.

With reference to FIGS. 12A to 12D, another embodiment of a tibial implant and an intermediate implant of an ankle prosthesis is shown. A tibial implant 805 and an intermediate implant 810 shown in FIGS. 12A to 12D are similar to those of described above for ankle prosthesis 10, except that the projecting member 830 and the implant lock 850 are different than those of the ankle prosthesis 10. In particular, the projecting member 830 comprises an circumscribing member 832 disposed around an inner core 834, where the circumscribing member 832 is composed of a material (e.g., stainless steel, titanium and its alloys, cobalt chrome alloys or any other biocompatible metal) that is capable of being permanently deformed by the implant lock 850. The circumscribing member 832 and the inner core 834 are configured such that they resist rotation relative to each other when coupled. Like in ankle prosthesis 10, the implant lock 850 can be inserted into a slot 860 in a direction that is perpendicular to the axis of rotation of the intermediate implant 810.

The implant lock 850 is configured to press into the circumscribing member 832 thereby permanently deforming the circumscribing member 832. For example, the implant lock 850 can define a threaded bore 855 configured to receive a screw 857. Rotating the screw 857 into the threaded bore 855 can force a moveable component 858 to extend and press into the circumscribing member 832. The pressure applied by the moveable component 858 can deform the circumscribing member 832, thereby causing the circumscribing member 832 to impede rotation of the intermediate implant 820 relative to the tibial implant 805.

A method of determining the relative position of a talar implant to a tibial implant while the implants are in the body can comprise determining whether an apex of the upper surface of the talar implant is posterior to, anterior to, or aligned with a center of a recess of the tibial implant. The center of the recess is the center of curvature of the curve along which the sidewall defining the recess extends. The method of determining the relative position of the two implants can comprise inserting a measurement tool into the recess of the tibial implant. An intermediate implant can be selected from amongst implants with varied projection member positions depending on whether the apex of the upper surface of the talar implant is posterior to, anterior to, or aligned with a center of a recess of the tibial implant.

Once an appropriate intermediate implant is selected, the implant can be inserted between the tibial implant and the talar implant such that the projecting member is disposed within the recess of the tibial implant. In some embodiments, the projecting member while disposed within the recess of the tibia implant is able to freely rotate within the recess.

A method of establishing the position of the intermediate implant relative to a tibial implant can comprise rotating the intermediate implant relative to the tibial implant and fixing the position of the intermediate implant relative to the tibial implant. Fixing the position of the intermediate implant comprises engaging an implant lock with the intermediate implant such that the implant lock resists rotation of the intermediate implant by applying a force that is only substantially perpendicular to the axis of rotation of the intermediate implant. The implant lock can be inserted into the ankle prosthesis along a direction that is substantially perpendicular to the axis of rotation of the intermediate implant. In some embodiments, only a portion of the implant lock is advanced toward the projecting member of the intermediate implant to engage the projecting member. This can occur while the tibial implant, the talar implant, and the intermediate implant are implanted in the ankle. In some embodiments, rotating the screw of the implant lock fixes the position of the intermediate implant relative to the tibial implant.

A method of inserting the ankle prosthesis can comprise inserting an implant lock into the ankle prosthesis along a direction that is substantially perpendicular to the axis of rotation of the intermediate implant (e.g., the axis of rotation that extends along the Z-Z axis shown in FIG. 2). In some embodiments, only a portion of the implant lock is advanced toward the projecting member of the intermediate implant in the substantially perpendicular direction to engage the projecting member. In some embodiments, rotating the screw of the implant lock fixes the position of the intermediate implant relative to the tibial implant.

A method of replacing an intermediate implant of an ankle prosthesis (such as that described above) can comprise accessing an ankle prosthesis within the patient, releasing a first intermediate implant from a locked position, removing the first intermediate implant from the ankle prosthesis, and inserting a second intermediate implant into the ankle prosthesis. In some embodiments, releasing the intermediate implant from a locked position can comprise removing a force that is only substantially perpendicular to the axis of rotation of the intermediate implant, such as by releasing/unlocking the implant lock. Unlocking the implant lock to release the intermediate implant can comprise rotating the screw of the implant lock. Once the first intermediate implant is removed and the second intermediate implant is inserted, the same or a second implant lock can be inserted into the ankle prosthesis. In some embodiments, the second intermediate implant is allowed to rotate relative to the tibial implant and then the position of the intermediate implant can be fixed relative to the tibial implant.

Figure 13:
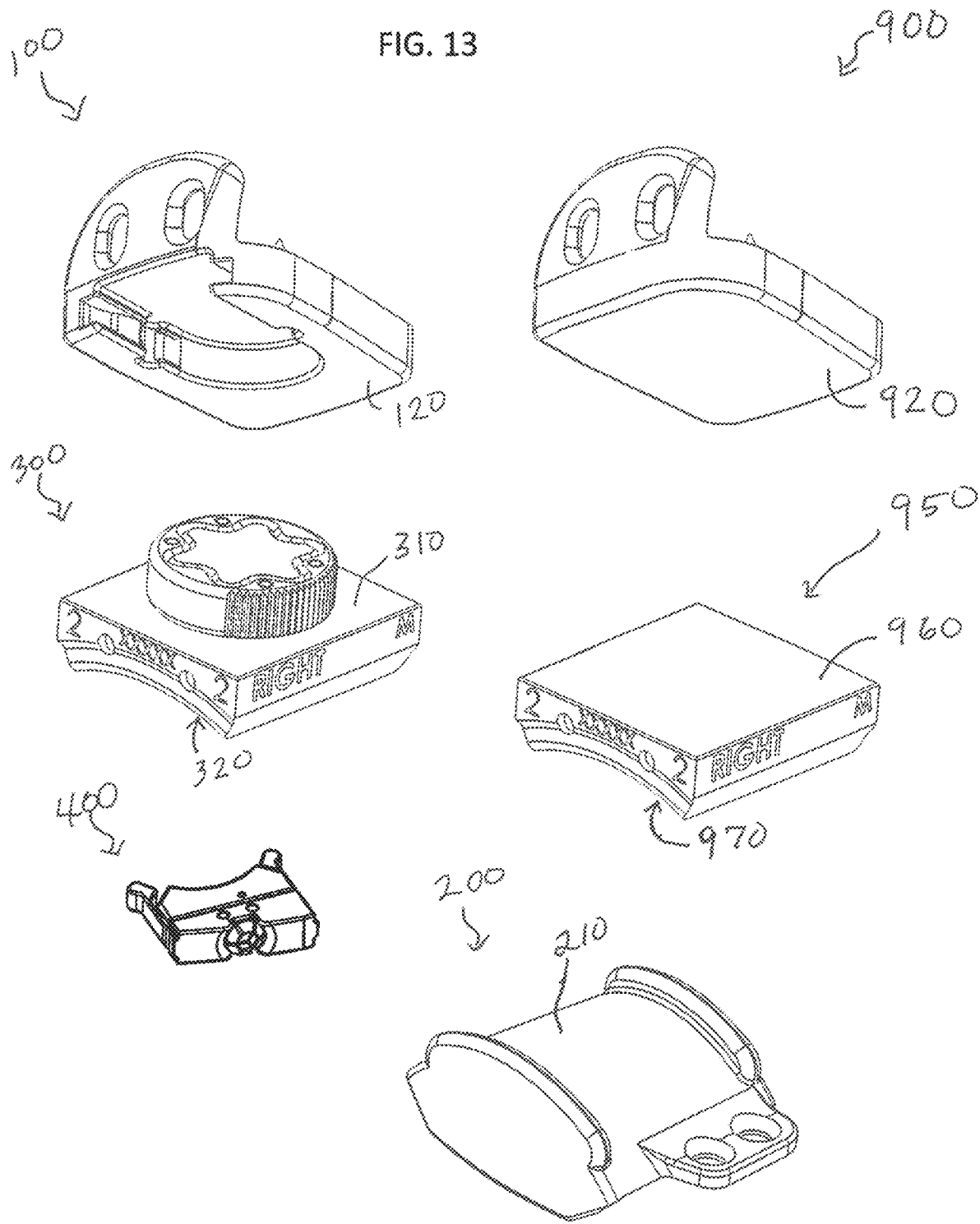
FIG. 13 illustrates an embodiment of ankle prosthesis kit.

Another aspect of the present disclosure pertains to an ankle prosthesis kit comprising a single talar implant configured for use in either a mobile bearing device or a fixed bearing device. Such kits can allow a surgeon to choose intraoperatively between implanting a mobile bearing device or a fixed bearing device. In an embodiment, as shown in FIG. 13, the kit can comprise one talar implant 200, an implant lock 400, and two different types of intermediate implants and tibial implants, namely, a first intermediate implant 300 and a first tibial implant 100 as well as a second intermediate implant 950 and a second tibial implant 900. The talar implant 200, the implant lock 400, the first intermediate implant 300, and the first tibial implant 100 are the same as those described above and shown in FIGS. 3, 4A, 4B, 6A, 6B, 8A to 8C and 10A to 10D. Both the first and second intermediate implants 300, 950 have identical lower bearing surfaces 320, 970, which are shaped to correspond to the upper bearing surface 210 of the talar implant 200. However, the upper surface contours 310, 960 of each intermediate implant 300, 950 are different. The first intermediate implant 300 is configured to couple in fixed relation to the first tibial implant 100 as described with respect to the embodiment shown in FIG. 3. The second intermediate implant 950 is configured to slide or rotate relative to the second tibial implant 900 and not couple in fixed relation thereto. As such, the upper bearing surface 960 of the second intermediate implant 950 is planar, and the lower bearing surface 920 of the second tibial implant 900 is also planar.

A system in which the talar implant 200 can be utilized in either a mobile-bearing or a fixed-bearing device, such as that described above and shown in FIG. 13, can also be useful in scenarios where one style of ankle prosthesis (mobile-bearing or fixed-bearing) is implanted into a patient but after some time, a determination is made to use the other style. In such circumstances, a revision arthroplasty procedure can be conducted that would leave the talar implant 200 in place but would swap the intermediate implant 300 or 950 and tibial implant 100 or 900 for those of the alternative style.

A method of implanting an ankle prosthesis can comprise implanting a talar implant 200 into a patient; selecting a tibial implant for implantation by choosing between a first tibial implant 100 configured to couple in fixed relation to a first intermediate implant 300 and a second tibial implant 900 being configured to be mobile bearing in relation to a second intermediate implant 950; implanting the selected tibial implant 100 or 900; selecting an intermediate implant for implantation by choosing between the first intermediate implant 300 and the second intermediate implant 950 based upon the selection of the tibial implant 100 or 900; implanting the selected intermediate implant 300 or 950, wherein both the first and second intermediate implants 300, 950 have a lower bearing surface 320, 970 that is shaped to correspond to an upper bearing surface 210 of the talar implant 200.

Embodiments described herein are useful in primary ankle replacements but can also be used in a revision arthroplasty procedure, including disarthrodesis.

Example Section

1. Ankle Prosthesis Wear Testing

Materials:

Four ankle prostheses for a right ankle were constructed in accordance with the present disclosure. The intermediate implant was composed of a UHMWPE and had a circumscribing member composed of Titanium alloy ASTM F136. The talar implant was composed of CoCr (ISO 5832/ASTM F75), and had a titanium and hydroxyapatite coating. The bearing surface of the talar implant is an 8 degree frustoconical-shaped surface. The tibial implant was composed of a titanium alloy ASTM F136. The implant lock insert was composed of titanium alloy ASTM F136 and the implant locking screw is composed of titanium alloy ASTM F136.

Equipment:

A servo hydraulic six station joint stimulator (Endolab, Rosenheim) was used for the wear testing. Three stations and one load-soak station were used.

Protocol:

All tests were performed in accordance with Endolab's TP-151109-2 (April 2017 as amended May 2017) using the parameters specified in Table 1 below.

TABLE 1

Figure 14:
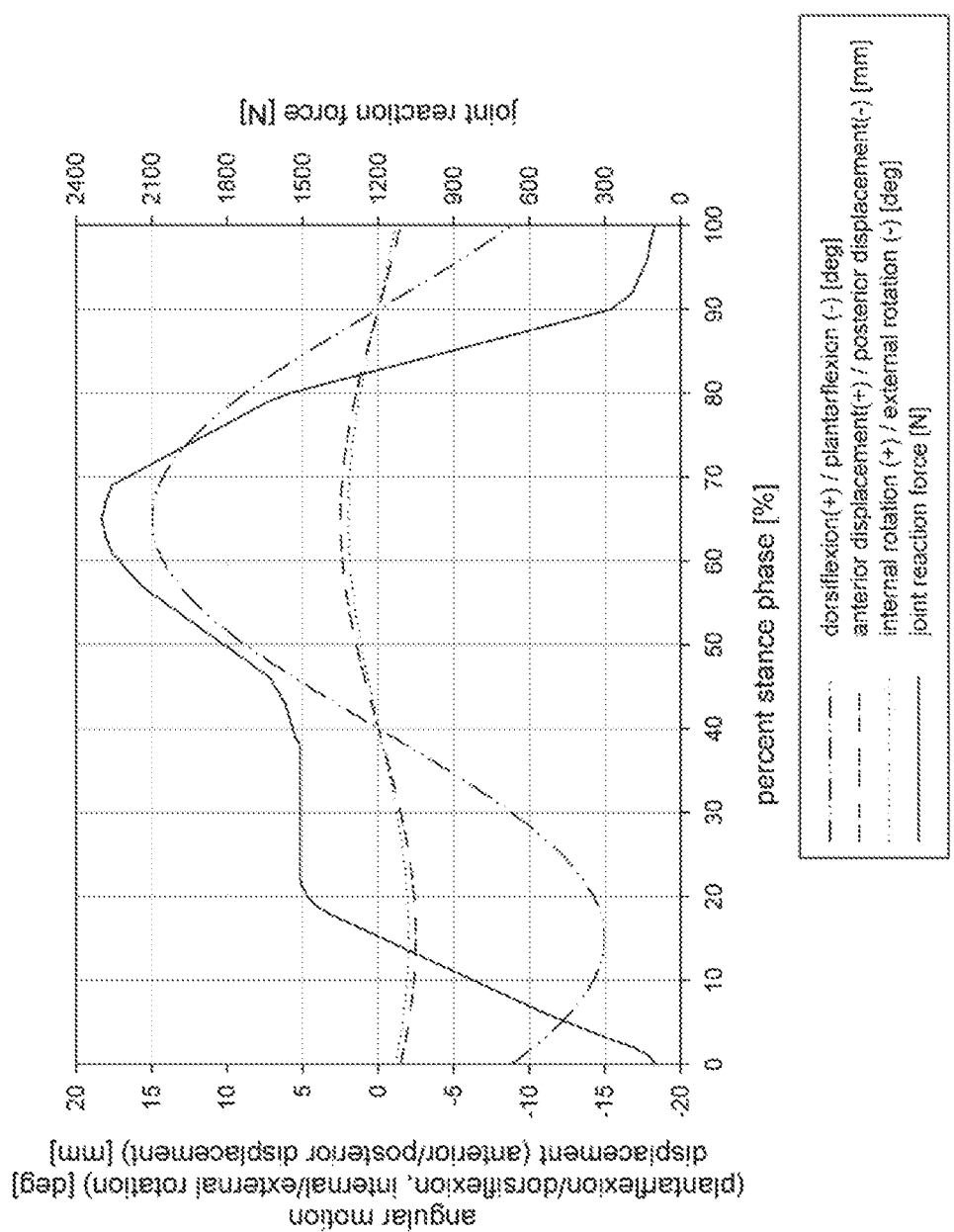
FIG. 14 is a graph of the kinematics and load profile which is an aspect of the wear test parameters described in the Example section.

| | |
|---|---|
| Force Curve | See FIG. 14 |
| Load direction was relative to the | tibial component |
| Force Maximum (joint reaction force) | 2.3 kN |
| Frequency | 1 Hz |
| Dorsiflexion/plantarflexion | +15°/−15° |
| internal rotation/external rotation | Not actively controlled but instead defined by the frustoconical surface of the talar implant and the intermediate implant corresponding to +/−2° internal/external rotation |
| displacement in anterior direction (+)/ displacement in posterior direction (−) | 2.5 mm/−2.5 mm |
| Test fluid temperature | 37° +/− 2° C. |
| Number of cycles | >9 million |
| Inspection cycles | every millionth cycle |

The test fluid was a calf serum diluted with deionized water to 20 grams of protein per liter with 2.3 g/l of EDTA, of 10 ml/l of amphotericin solution (250 µg/ml), and 10 ml/l of gentamicin solution (10 mg/ml).

All intermediate implants were presoaked in a test fluid for a period of 27 days. The test fluid was held at a temperature between 35° and 39° C.

For the load-soak control and the test articles, the test fluid was replaced every 500,000 cycles. The load-soak control underwent the same joint reaction force as the other samples but did not undergo any translational/angular motion.

When installing a sample into the simulator, the intermediate implant was locked to the tibial implant by tightening the implant lock screw to a torque of 1 Nm.

Samples are dismounted, inspected for wear, and cleaned every 0.5 million cycles, 1 million cycles, and at 1 million cycle intervals thereafter. The wear of the intermediate implant was determined according to gravimetric change of the component according to ISO 14243-2: 2016.

Results:

The data collected from the three wear samples was corrected by the weight loss of the load-soak control. After such correction, a mean wear rate of 1.38 mg per million cycles was observed between 0 and 9 million cycles for the three samples (SDev=0.08 mg per million cycles).

Visual inspection revealed that the teeth on the circumscribing member and the corresponding implant lock did not change in appearance throughout testing indicating that the tibial implant and the intermediate implant remained secure throughout the testing.

All three ankle prosthesis samples were still mechanically sound after 9 million cycles.

Similar wear testing was conducted on the mobile-bearing design shown in FIG. 13. The data collected from the three mobile-bearing wear samples was corrected by the weight loss of the load-soak control. After such correction, a mean wear rate of 2.62 mg per million cycles was observed between 0.5 and 5 million cycles for the three samples (SDev=0.17 mg per million cycles).

All three mobile-bearing ankle prosthesis samples were still mechanically sound after 5 million cycles.

2. Static Torque Testing

An ankle prosthesis as described in Example 1 was constructed. The intermediate implant was coupled to the tibial implant with the implant lock. Static torque was applied to the intermediate implant. The amount of torque was well above the amount that would be encountered during use by the full range of potential patients. Visual inspection revealed that the teeth on the circumscribing member and the corresponding implant lock did not change in appearance throughout testing indicating that the tibial implant and the intermediate implant remained secure throughout the testing.

3. Dynamic Anterior Force Testing

An ankle prosthesis as described in Example 1 was constructed. The ankle prosthesis as shown in FIG. 1 was assembled and secured to a stand. A dynamic force in a posterior to anterior direction was applied to the intermediate implant for 10,000 cycles. The maximum of the dynamic force was well above the amount that would be encountered during use by the full range of potential patients. Visual inspection revealed that the teeth on the circumscribing member and the corresponding implant lock did not change in appearance throughout testing indicating that the tibial implant and the intermediate implant remained secure throughout the testing.

Although embodiments described herein are made with reference to example embodiments, it should be appreciated by those skilled in the art that various modifications are well within the scope and spirit of this disclosure. Those skilled in the art will appreciate that the example embodiments described herein are not limited to any specifically discussed application and that the embodiments described herein are illustrative and not restrictive. From the description of the example embodiments, equivalents of the elements shown therein will suggest themselves to those skilled in the art, and ways of constructing other embodiments using the present disclosure will suggest themselves to practitioners of the art. Therefore, the scope of the example embodiments is not limited herein.

What is claimed is:

1. An ankle prosthesis comprising:
   a) a tibial implant;
   b) an intermediate implant comprising a first surface and a second, curved surface opposite the first surface and a projecting member extending outwardly from the first surface, wherein the projecting member is configured to extend into a recess of the tibial implant and rotate relative to the tibial implant, and
   c) an implant lock positioned anterior to the projecting member of the intermediate implant, the implant lock configured to resist rotation of the projecting member relative to the tibial implant by applying a force that is substantially perpendicular to the axis of rotation of the projecting member.

2. The ankle prosthesis of claim 1, wherein the projecting member can freely rotate relative to the tibial implant when disposed in the recess or wherein the projecting member can rotate at least 70 degrees, at least 180 degrees, or 360 degrees relative to the tibial implant when disposed in the recess.

3. The ankle prosthesis of claim 1, where the projecting member comprises a substantially circular transverse cross-section and a cross section of the projecting member perpendicular to the transverse cross-section that is a quadrilateral.

4. The ankle prosthesis of claim 1, wherein the projecting member comprises a lateral surface that is substantially parallel to the axis of rotation of the projecting member and has one or more interlocking surface features configured to engage with the implant lock.

5. The ankle prosthesis of claim 1, wherein the projecting member comprises a lateral surface having one or more interlocking surface features and wherein the implant lock comprises a first end and a second end opposite the first end, wherein the first end comprises one or more interlocking surface features configured to engage the one or more interlocking surface features of the lateral surface of the projecting member to resist rotation of the projecting member relative to the tibial implant.

6. The ankle prosthesis of claim 1, wherein the tibial implant defines a slot that is in communication with the recess and is configured such that the implant lock is inserted into the slot along a direction that is within 10° of an axis perpendicular to the axis of rotation of the projecting member.

7. The ankle prosthesis of claim 6, wherein the implant lock is configured to releasably interlock with a portion of the tibial implant.

8. The ankle prosthesis of claim 7, wherein the implant lock comprises a protrusion configured to engage with a notch in a sidewall of the slot such that the implant lock is releasably interlocked with the slot.

9. The ankle prosthesis of claim 8, wherein the implant lock comprises surface contours configured for gripping.

10. The ankle prosthesis of claim 8, wherein the slot has a width and the implant lock has a width that is less than the width of the slot.

11. The ankle prosthesis of claim 1, wherein the implant lock comprises an insert, the insert comprising a first portion and a second portion, wherein the first portion is moveable relative to the second portion.

12. The ankle prosthesis of claim 11, wherein the implant lock comprises a screw and wherein the insert comprises a bore configured to receive the screw.

13. The ankle prosthesis of claim 12, wherein the first portion and the second portion are configured to move away from each other as the screw is rotated in a first direction and toward each other as the screw is rotated in a second direction.

14. The ankle prosthesis of claim 1, wherein the projecting member comprises an inner core of a first material and a circumscribing member of a second material, wherein the second material is higher modulus than the first material.

15. The ankle prosthesis of claim 14, wherein the inner core is coupled in fixed relation to the circumscribing member.

16. The ankle prosthesis of claim 15, wherein the inner core has a non-circular, transverse cross-sectional shape and the circumscribing member defines an interior opening that has a transverse cross-sectional shape that is the same as the transverse cross-sectional shape of the innercore.

17. An ankle prosthesis comprising:
   a) a tibial implant, wherein the tibial implant defines a recess and a slot, wherein the slot is in communication with the recess;
   b) an intermediate implant comprising a first surface and a second, curved surface opposite the first surface and a projecting member extending outwardly from the first surface, wherein the projecting member is configured to extend into the recess of the tibial implant and rotate relative to the tibial implant, and
   c) a removable implant lock configured to be at least partially disposed within the slot and to resist rotation of the projecting member relative to the tibial implant, wherein the slot is configured such that the implant lock is inserted into the slot along a direction that is within 10° of an axis perpendicular to the axis of rotation of the projecting member.

18. The ankle prosthesis of claim 17, wherein the projecting member comprises a lateral surface and where the implant lock is configured to engage with the lateral surface of the projecting member such that rotation of the projecting member is resisted.

19. An ankle prosthesis comprising:
   a) a tibial implant;
   b) an intermediate implant comprising a first surface and a second, curved surface opposite the first surface and a projecting member extending outwardly from the first surface, wherein the projecting member is configured to be disposed in a recess of the tibial implant and rotate relative to the tibial implant, and
   c) an implant lock configured to move in the anterior-posterior direction relative to the projecting member and configured to resist rotation of the projecting member relative to the tibial implant,
   wherein the projecting member comprises a lateral surface, where the implant lock is configured to engage with the lateral surface of the projecting member such that rotation of the projecting member is resisted, wherein the projecting member comprises a first end and a second end opposite the first end and the lateral surface extends between the first and second end, wherein the first end is closer to the first surface of the intermediate implant than the second end.

20. An ankle prosthesis comprising:
a) a tibial implant;
b) an intermediate implant comprising a first surface and a second, curved surface opposite the first surface and a projecting member extending outwardly from the first surface, wherein the projecting member is configured to extend into a recess of the tibial implant and rotate relative to the tibial implant, and
c) an implant lock configured to resist rotation of the projecting member relative to the tibial implant, wherein the implant lock traverses linearly in a direction substantially perpendicular to the axis of rotation of the projecting member to engage the projecting member thereby resisting the rotation of the projecting member.

* * * * *